United States Patent
Kumar et al.

(10) Patent No.: US 10,421,769 B2
(45) Date of Patent: Sep. 24, 2019

(54) ANTICANCER PROPERTY STUDIES OF CHIRAL PALLADIUM N-HETEROCYCLIC CARBENE COMPLEXES AND PROCESS FOR PREPARATION THEREOF

(71) Applicant: Indian Institute of Technology Bombay, Mumbai (IN)

(72) Inventors: Anuj Kumar, Mumbai (IN); Afsana Naaz, Mumbai (IN); Prakasham Ayyampudur Palanisamy, Mumbai (IN); Dulal Panda, Mumbai (IN); Prasenjit Ghosh, Mumbai (IN)

(73) Assignee: India Institute of Technology Bombay, Mumbai (IN)

( * ) Notice: Subject to any disclaimer, the term of this patent is extended or adjusted under 35 U.S.C. 154(b) by 0 days.

(21) Appl. No.: 15/806,889

(22) Filed: Nov. 8, 2017

(65) Prior Publication Data
US 2018/0194789 A1 Jul. 12, 2018

(30) Foreign Application Priority Data
Jan. 7, 2017 (IN) .............................. 201721000741

(51) Int. Cl.
C07F 15/00 (2006.01)
A61P 35/00 (2006.01)

(52) U.S. Cl.
CPC ............ C07F 15/006 (2013.01); A61P 35/00 (2018.01)

(58) Field of Classification Search
None
See application file for complete search history.

(56) References Cited

PUBLICATIONS

Kumar et al., Inorg. Chem., 2016, 55, 6, 2882-2893.*
Angew. Chem. Int. Ed. 2007, 46, 2768-2813, Palladium Complexes of N-Heterocyclic Carbenes as Catalysts for Cross-Coupling Reactions—A Synthetic Chemist's Perspective.
Chem. Soc. Rev., 2015, 44, 8773, Multi-platinum anti-cancer agents. Substitution-inert compounds for tumor selectivity and new targets.
(Continued)

*Primary Examiner* — Alicia L Otton
(74) *Attorney, Agent, or Firm* — The Dobrusin Law Firm, PC

(57) ABSTRACT

The present invention relates to the anticancer property studies of a series of chiral palladium N-heterocyclic carbene complexes of the general formula of $(NHC)_2PdX_2$ [NHC=chiral N-heterocyclic carbene ligand 1-(1S,2S,5R/1R,2R,5S)-menthyl-4-(R)-1,2,4-triazol-5-ylidene, wherein R=Et, allyl and $CH_2Ph$; X=Br or $OCOCF_3$], as designated by, (1S,2S,5R)-(1-3)b and (1R,2R,5S)-(1-3)b, (1S,2S,5R)-(1, 3)c and (1R,2R,5S)-(1, 3)c represented by formula (Ig, Ih) below.

Formula (Ig, Ih)

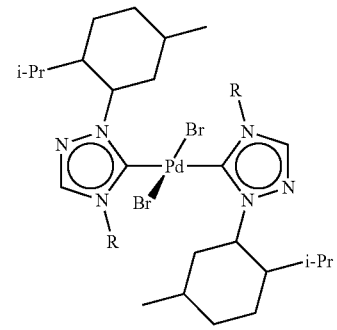

Figure 1:
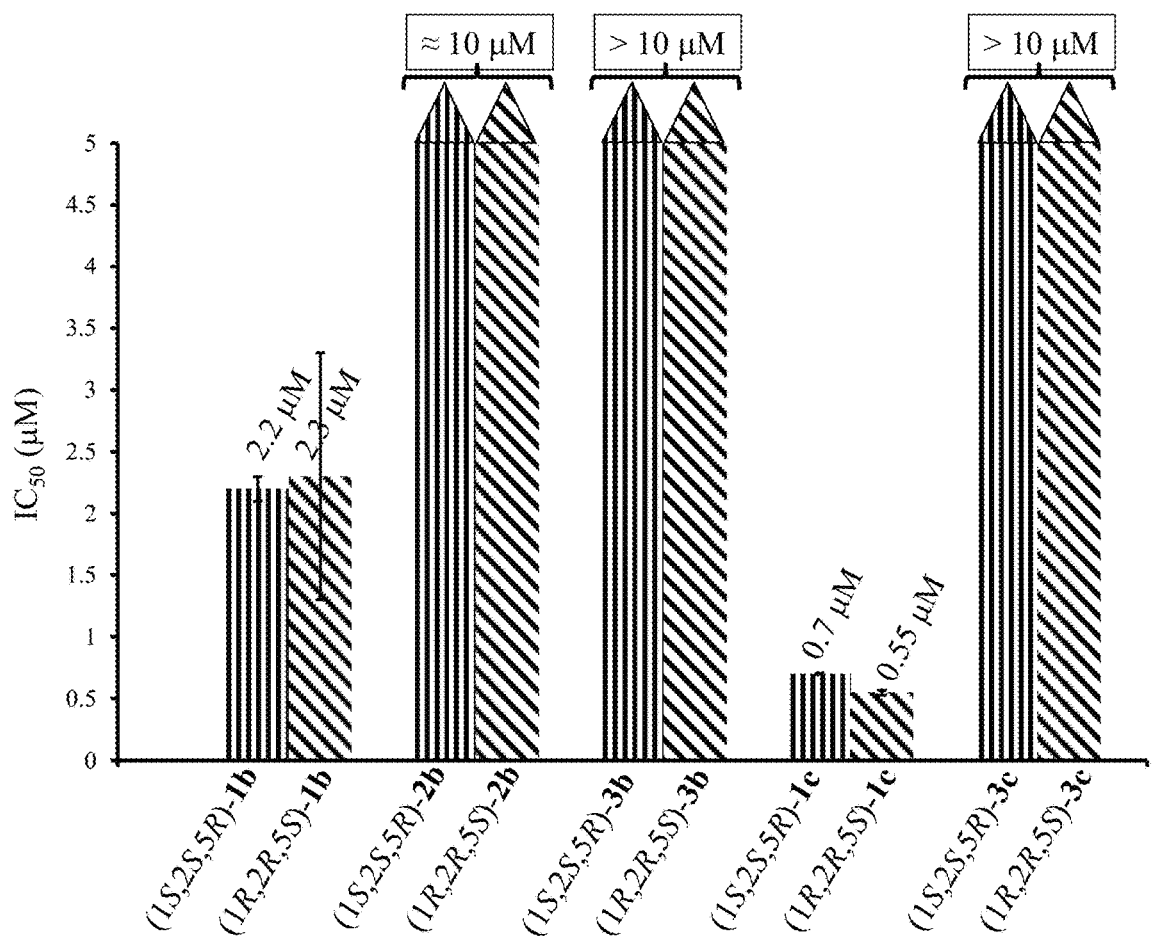

(1S,2S,5R)-(1-3)b
(1R,2R,5S)-(1-3)b

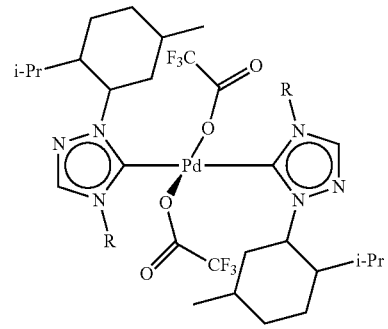

(1S,2S,5R)-(1c & 3c)
(1R,2R,5S)-(1c & 3c)
R = Et (1), allyl (2), $CH_2Ph$ (3)

The present invention further investigates the influence of chirality on the anticancer activity, wherein the enantiomeric pairs of present chiral palladium N-heterocyclic carbene complexes of formula (Ig, Ih) shows no differential activity based on optical isomerism despite all of the palladium complexes exhibiting high anti-proliferative activity towards a variety of cancer cells. Also, provided herein is a process of preparation of the chiral palladium N-heterocyclic carbene complexes and a pharmaceutical composition comprising the chiral palladium N-heterocyclic carbene complexes. The present invention relates to the mechanistic details highlighting the mode of action of the chiral palladium N-heterocyclic carbene complex of the formulation for their anticancer application.

24 Claims, 9 Drawing Sheets

(56) References Cited

PUBLICATIONS

Chem. Soc. Rev., 2013, 42, 755, Metal N-heterocyclic carbene complexes as potential antitumor metallodrugs.
J. Organomet, Chem 694 (2009) 2328-2335, Design of Nickel Chelates of Tetradentate N-heterocyclic carbenes with subdued cytotoxicity.
Metallomics, 2013, 5, 760, Sterically tuned (ag(i)- and Pd(ii)-N-heterocyclic carbene complexes of imidazole-2-ylidenes: synthesis, crystal structures, and in vitro antibacterial and anticancer studies.
Angew. Chem. 2016, 128, 12114-12118, Cyclometalated Palladium(II) N-Heterocyclic Carbene Complexes: Anticancer Agents for Potent in Vitro Cytotoxicity and in Vivo Tumor Growth Suppression.
CA Cancer J Clin 2016, 66:7-30, Cancer Statistics.
J. National Cancer Inst. 1990, 82, 1107, New Colorimetric Cytotoxicity Assay for Anticancer-Drug Screening.
New J. Chem., 2016, 40, 1063, Recent advances in iron complexes as potential anticancer agents.
ACS Omega, 2017, 2 4632-4646, Potent Anticancer Activity with High Selectivity of a Chiral Palladium N-Heterocyclic Carbene Complex.
AM. J. Med. Sci, 2007, 334, 115-124, Cisplatin Nephrotoxicity: A Review.
Cancer Treat. Rev., 2007, 33, 9-23, Molecular mechanisms of resistance and toxicity associated with platinating agents.
Chem. Soc. Rev., 2014, 43, 4751-4777, Anti-cancer palladium complexes: a focus on $PdX_2L_2$, palladacycles and related complexes.
Dalton Transactions, 2010, 39, 8113-8127, the status of platinum anticancer drugs in the clinic and in clinical trials.
Int. J. Pharma Res. Rev, 2015; 4, 59-66, Metal Ion Complex-potential Anticancer Drug—a Review.
J. Am. Chem. Soc. 2007, 129, 15048, Anticancer and Antimicrobial Metallopharmaceutical Agents Based on Palladium, Gold, and Silver N-Heterocyclic Carbene Complexes.
Kidney Int., 2008, 73, 994-1007, Cisplatin nephrotoxicity: Mechanisms and renoprotective Strategies.
Organometallics 2004, 23, 15, 3752-3755, N-Heterocyclic Carbene Palladium Complexes Bearing Carboxylate Ligans and Their Catalytic Activity in the Hydroarylation of Alkynes.
WHO Fact Sheet No. 297, Feb. 2015, WHO fact sheet on Cancer (updated on $25^{th}$ Feb. 2015).

\* cited by examiner

ANTICANCER PROPERTY STUDIES OF CHIRAL PALLADIUM N-HETEROCYCLIC CARBENE COMPLEXES AND PROCESS FOR PREPARATION THEREOF

FIELD OF INVENTION

The present invention relates to a series of chiral palladium N-heterocyclic carbene complexes, particularly to the compounds of the formulation $(NHC)_2PdX_2$ (NHC=1-(1S, 2S,5R/1R,2R,5S)-menthyl-4-(R)-1,2,4-triazol-5-ylidene, where R=Et, allyl and $CH_2Ph$; X=Br or $OCOCF_3$, and represented by Formula (Ig, Ih) below:

Formula (Ig, Ih)

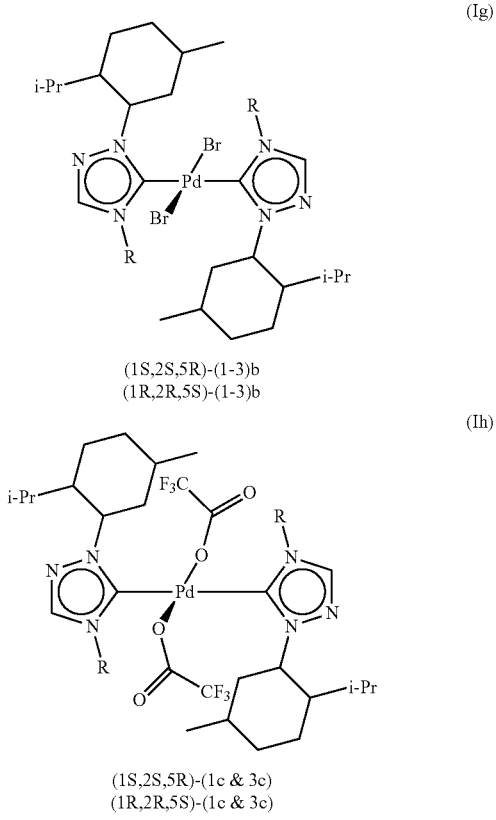

(1S,2S,5R)-(1-3)b
(1R,2R,5S)-(1-3)b (1S,2S,5R)-(1c & 3c)
(1R,2R,5S)-(1c & 3c)

R = Et (1), allyl (2), $CH_2Ph$ (3)

BACKGROUND AND PRIOR ART OF INVENTION

Cancer is one of the most widespread and dreaded diseases in the world today. It is feared largely because it is known to be difficult to cure, since, cancer results from the uncontrolled multiplication of imperceptibly modified normal human cells. Cancer claims maximum loss of human lives worldwide annually. Thus the fight against cancer still remains an open cause requiring determined pursuits (WHO fact sheet No 297, February 2015; Siegel, R. L.; Miller, K. D.; Jemal, A. C A. *Cancer J. Clin.,* 2016, 66, 7-30).

Among several strategies invoked in battling the cancer, chemotherapy, involving targeting the cancer cells with transition metal complexes, remains a popular approach (Wani, W. A.; Baig, U.; Shreaz, S.; Shiekh, R. A.; Iqbal, P. F.; Jameel, E.; Ahmad, A.; MohdSetapar, S. H.; Mushtaqueh, M.; Hun. L. T. *New. J. Chem.,* 2016, 40, 1063-1090; Liu. W.; Gust, R. *Chem. Soc. Rev.,* 2013, 42, 755-773; Page, S. *Educ. Chem.,* 2012, 49, 26-29). Thus, recent advances in medicinal inorganic chemistry give significant prospects for the utilization of metal complexes in the development of anticancer drugs (Baile M. B et. al.: *International Journal of Pharma Research & Review,* August 2015; 4(8):59-66).

Though numerous transition metal complexes are known to exhibit anticancer properties, the platinum (Pt) based blockbuster drug, Cisplatin inhibits cancer cell proliferation by binding to DNA inside the nucleus of a cancer cell. In 1960, the anti-tumor activity of an inorganic complex cis-diammine-dichloroplatinum (II) (Cisplatin) was discovered. Since then, Cisplatin has developed into becoming the most successful drug against carcinoma (Farrell, N. P.; *Chem. Soc. Rev.,* 2015, 44, 8773-8785; Wheate, N. J.; Walker, S.; Craig, G. E.; Oun, R. *Dalton Trans.,* 2010, 39, 8113-8127). Despite the popularity, Cisplatin suffers from limitations arising from its low solubility, leading to inconvenient intravenous administration of the drug, various toxicity issues and the gradual acquired resistance of the cancer cells against the drug, thus adding to the need for alternative metallodrugs for cancer therapy (Pabla, N.; Dong, Z. *Kidney Int.,* 2008, 73, 994-1007; Rabik, C. A.; Dolan, M. E. *Cancer Treat. Rev.,* 2007, 33, 9-23; Yao, X.; Panichpisal, K.; Kurtzman, N.; Nugent, K. *Am. J. Med. Sci.,* 2007, 334, 115-124).

In view of the aforementioned disadvantages of using Pt based metallodrug Cisplatin, there is a need in the relevant art to develop other active metallodrugs, as anti-cancer actives. Ghosh, P. et. al.: *J. Organomet. Chem.* 2009, 694, 2328-2335 discloses the reduced toxicity of chelated nickel N-heterocyclic carbene complexes bearing potential utility as immunotolerance agents. Pd based N-heterocyclic carbene (in short "NHC") metal complexes that are known in the art are as catalytically active ligands (Organ et. al.: *Angew. Chem. Int. Ed.* 2007, 46, 2768-2813; Nolan et. al: *Organometallics* 2004, 23, 3752-3755), Recently, some Pd—NHC metal complexes have been designed and reported to have anti-cancer properties. Ghosh, P. et. al.: *J. Am. Chem. Soc.* 2007, 129, 15042-15053 discloses anticancer activities of the imidazole based Pd—NHC complexes; Haque et. al.: *Metallomics,* 2013, 5, 760-769 reveals chlorine (Cl)—Pd—NHC complex mimicking Pt-based NHC complexes like Cisplatin and its superior anti-cancer activity over Cisplatin; review article Kapdi et. al: *Chem. Soc. Rev.,* 2014, 43, 4751-4777 reports that Cl—Pd—NHC, show anti-tumour activity against three human tumour cells namely cervical cancer (HeLa), breast cancer (MCF-7), and colon adenocarcinoma (HCT 116).

Selectivity towards the cancer cells as opposed to its normal counterparts is an important marker of a potent anticancer compound. In this regard, Che. C. M. et al, discloses less cytotoxicity of a cyclometalated palladium N-heterocyclic carbene complex toward the normal human fibroblast cell line (CCD-19Lu, IC50=11.8 μm) (Che. C. M. et al, *Angew. Chem.* 2016, 128, 12114-12118).

Lastly, the gradual acquired resistant towards anticancer drugs is an important issue to resolve for designing an effective drug. Thus, bearing all of the aforementioned issues of the selectivity, the mechanistic understanding and that of the gradual acquired resistant towards anticancer drugs, there is a long-standing requirement of having highly effective anticancer activities of such Pd—NHC compounds. Hence, there is still a need in the art to develop active Pd—NHC metal complexes with enhanced therapeutic anti-cancer potency in comparison to those reported in the above prior arts.

Accordingly, the present inventors have developed chiral compounds of a series of enantiomeric pairs of palladium N-heterocyclic carbene (Pd—NHC) complexes with high potency anti-cancer activities.

OBJECTIVES OF THE INVENTION

It is an object of the present invention to overcome the drawbacks of the prior art.

It is another object of the present invention to provide a series of chiral palladium N-heterocyclic carbene (Pd—NHC) metal complex of general formula (I) below, having high anti-cancer activities in in vitro.

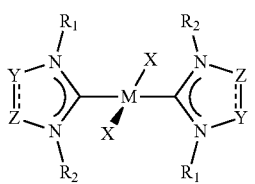
(I)

It is another object of the present invention to provide chiral palladium N-heterocyclic carbene complexes of particular formulation $(NHC)_2PdX_2$ (NHC=1-(1S,2S,5R/1R,2R,5S)-menthyl-4-(R)-1,2,4-triazol-5-ylidene, where R=Et, allyl and $CH_2Ph$; X=Br or $OCOCF_3$, represented by formula (Ig, Ih) below:

Formula (Ig, Ih)

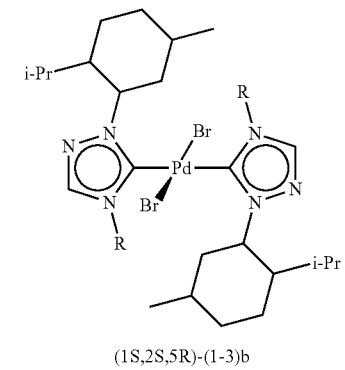

(1S,2S,5R)-(1-3)b
(1R,2R,5S)-(1-3)b

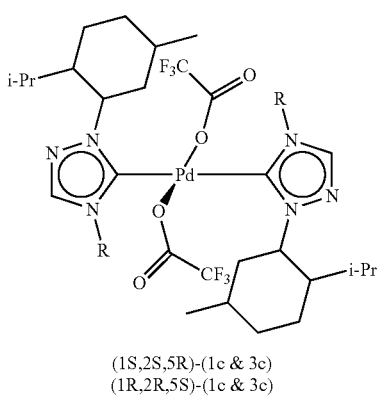

(1S,2S,5R)-(1c & 3c)
(1R,2R,5S)-(1c & 3c)
R = Et (1), allyl (2), $CH_2Ph$ (3)

It is another object of the present invention to study the influence of chirality on the anticancer properties of enantiomeric pairs of $(NHC)_2MX_2$ (wherein, M is Pd, X is Br or OCOCF3) type chiral metal complexes of general formula (I) above, along with enhancement of the anticancer properties of these palladium N-heterocyclic carbene (Pd—NHC) complexes achieved through incorporation of polar functionality within the metal complexes.

It is another object of the present invention to provide a process for preparation of the enantiomeric pairs of present $(NHC)_2MX_2$ (wherein, M is Pd, X is Br or $OCOCF_3$) type chiral metal complexes of general formula (I) above.

It is another object of the present invention to provide a pharmaceutical composition comprising of present $(NHC)_2MX_2$ (wherein, M is Pd, X is Br or $OCOCF_3$) type chiral metal complexes of general formula (I) above, along with a pharmaceutically acceptable excipient.

It is another object of the present invention to provide a pharmaceutical composition comprising of present $(NHC)_2MX_2$ (wherein, M is Pd, X is Br or $OCOCF_3$) type chiral metal complexes of general formula (I) above, for treating breast cancer, cervical cancer, lung cancer, skin cancer and multidrug resistant cancer.

It is another object of the present invention to provide selectivity towards the cancer cells as opposed to its normal counterparts.

It is another object of the present invention to provide mode of action and mechanistic insights on the $(NHC)_2MX_2$ (wherein, M is Pd, X is Br or $OCOCF_3$) type chiral metal complexes of general formula (I) in the treatment of cancer.

SUMMARY OF THE INVENTION

An aspect of the present invention provides a chiral N-heterocyclic carbene complex of formula (I):

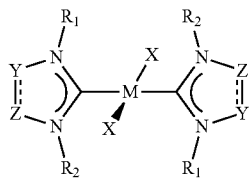
(I)

wherein,
M is palladium;
X is a monoanionic ligand selected from Br or $OCOCF_3$;
$R_1$ is a substituted or unsubstituted chiral hydrocarbyl selected from a group consisting of (1S) menthyl, (1R) menthyl, (1S,2S,5R) 2-i-propyl-5-methylcyclohexyl, (1R,2R,5S) 2-i-propyl-5-methylcyclohexyl, (1S)-pinane and (1R)-isobornyl;
$R_2$ is selected from a group consisting of C1-C10 alkyl, allyl, aryl, heterocyclyl, alkylheterocyclyl;
Y or Z is N, CH or $CH_2$, with the proviso that any one of Y or Z is always N.

Another aspect of the present invention provides a process for preparation of the enantiomeric pairs of N-heterocyclic carbene complex of the present invention which comprises steps of: (a) converting a chiral alcohol using a tosylating agent so as to make a leaving group; followed by a (b) nucleophilic substitution reaction of the tosylated chiral hydrocarbyl formed in step 'a' with a heterocyclic compound by a suitable base; (c) N-alkylation of the compound formed in step 'b' with selective alkyl halides to give respective azolium salts; (d) directly reacting the formed azolium salts with a metallic salt $MX_2$, wherein M is Pd, X is a monoanionic ligand selected from Br, Cl, I or $OCOCH_3$, in presence of a suitable base under reflux conditions forming $(NHC)_2MX_2$ type chiral precursors; followed by (e) a metal salt metathesis reaction of said $(NHC)_2MX_2$ type chiral precursors, wherein M is Pd, X is selected from Br, Cl, I or $OCOCH_3$, with M'nYn, wherein M' is any metal, Y is any anionic ligand preferably $OCOCF_3$, n is 1 or 2, under stirring in room temperature.

Another aspect of the present invention provides a pharmaceutical composition comprising the chiral N-heterocyclic carbene complex of the present invention, along with a pharmaceutically acceptable excipient.

A further aspect of the present invention provides a method of treating cancer comprising administering the chiral N-heterocyclic carbene complex or the pharmaceutical composition of the present invention.

BRIEF DESCRIPTION OF ACCOMPANYING DRAWINGS

FIG. 1 graphically demonstrates the anticancer activity of the present $(NHC)_2PdX_2$ type complexes where X is Br or $OCOCF_3$ against MCF-7 cell lines.

Figure 2:
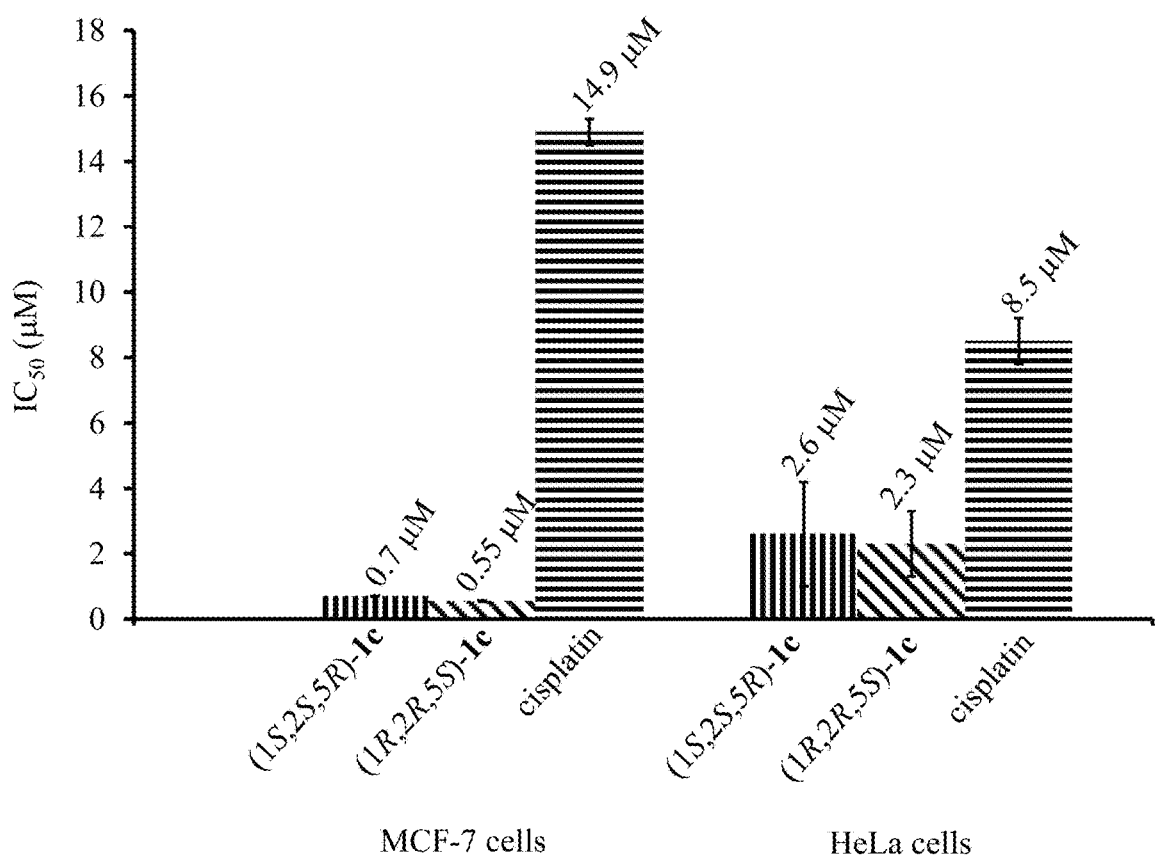

FIG. 2 graphically compares the anticancer activity of the most potent Pd—NHC complexes (1S,2S,5R)-1c and (1R,2R,5S)-1c of the present invention against MCF-7 and HeLa cell lines with the benchmark drug Cisplatin.

Figure 3:
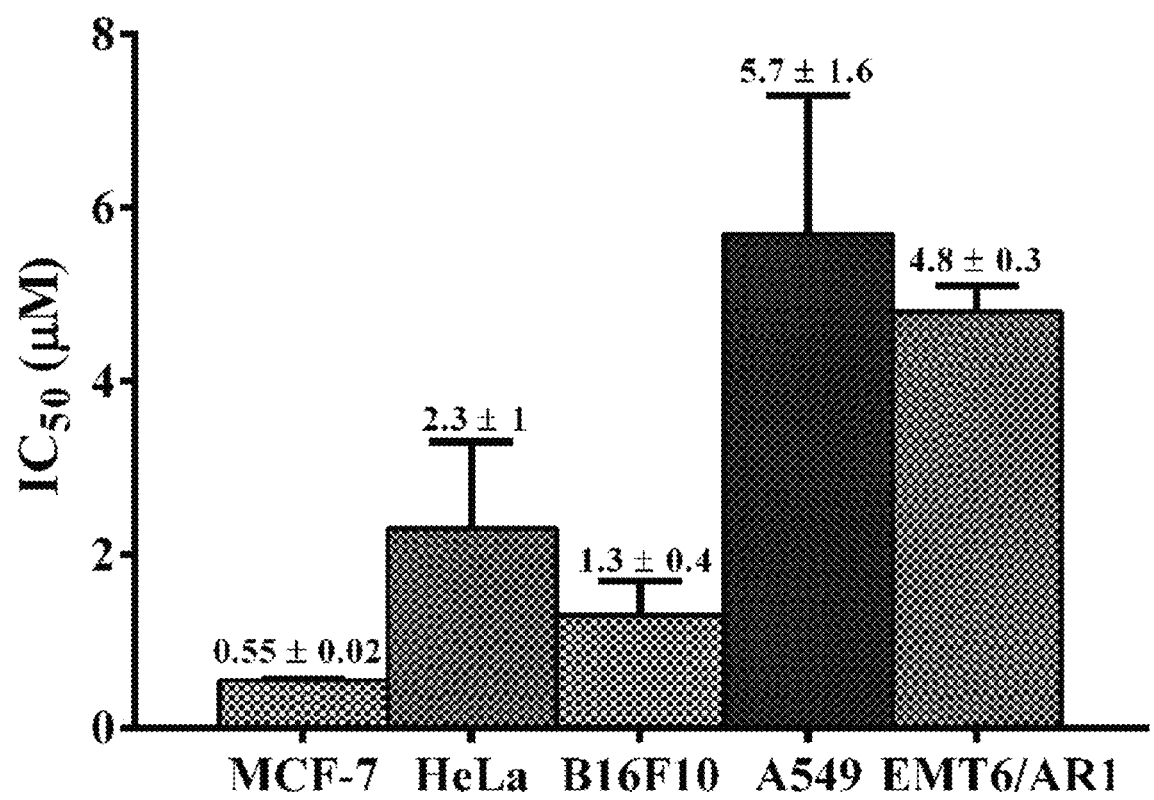

FIG. 3 graphically demonstrates the anticancer activity of the potent Pd—NHC complex (1R,2R,5S)-1c of the present invention against various cancer cell lines namely human breast cancer cells (MCF-7), human cervical cancer cells (HeLa), human lung cancer cells (A549), mouse skin cancer cells (B16-F10) and the multidrug resistant mouse mammary cancer cells (EMT6/AR1).

Figure 4:
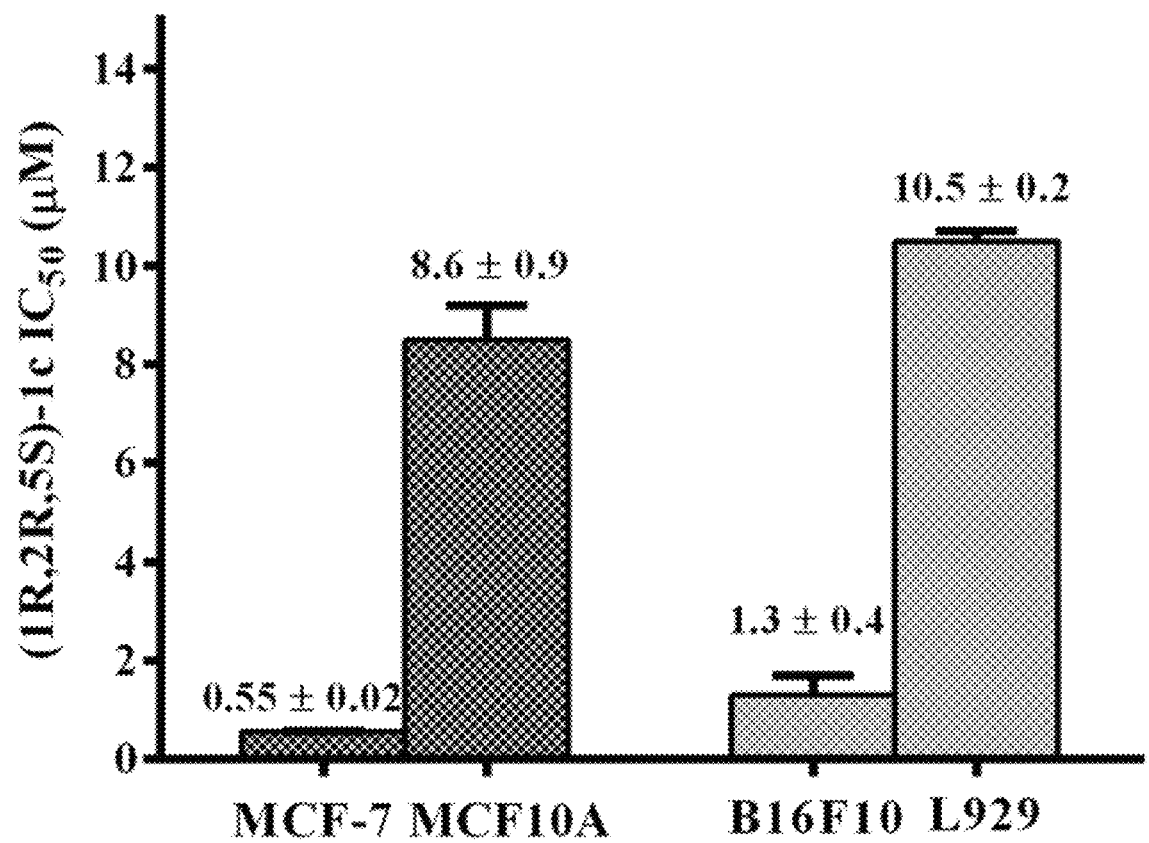

FIG. 4 graphically demonstrates the selectivity of the potent complex (1R,2R,5S)-1c against the cancer cell lines, MCF-7 and B16-F10 and their respective noncancerous counterparts, MCF10A and L929.

Figure 5A:
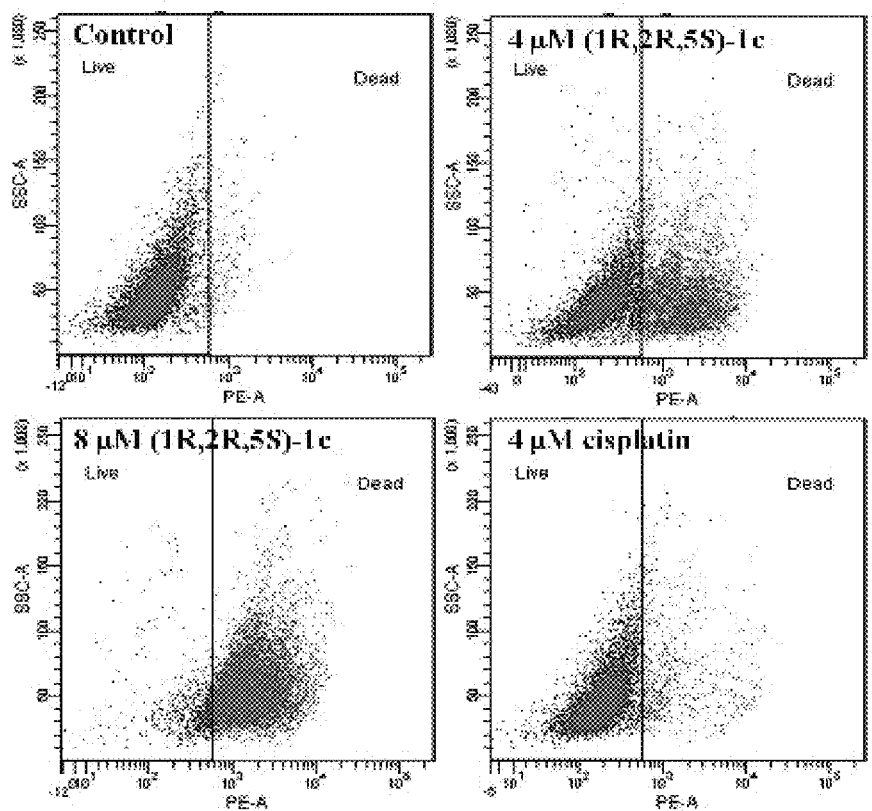

FIG. 5A graphically demonstrates (1R,2R,5S)-1c treatment leads to cell death in MCF-7 cells.

Figure 5B:
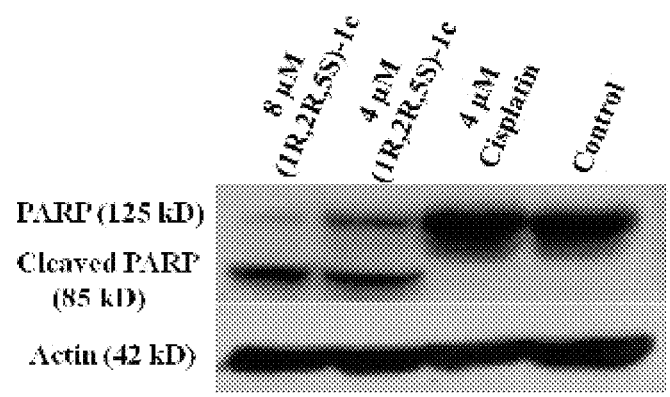

FIG. 5B graphically demonstrates (1R,2R,5S)-1c cleaves PARP in MCF-7 cells indicating apoptosis of cells.

Figure 6A:
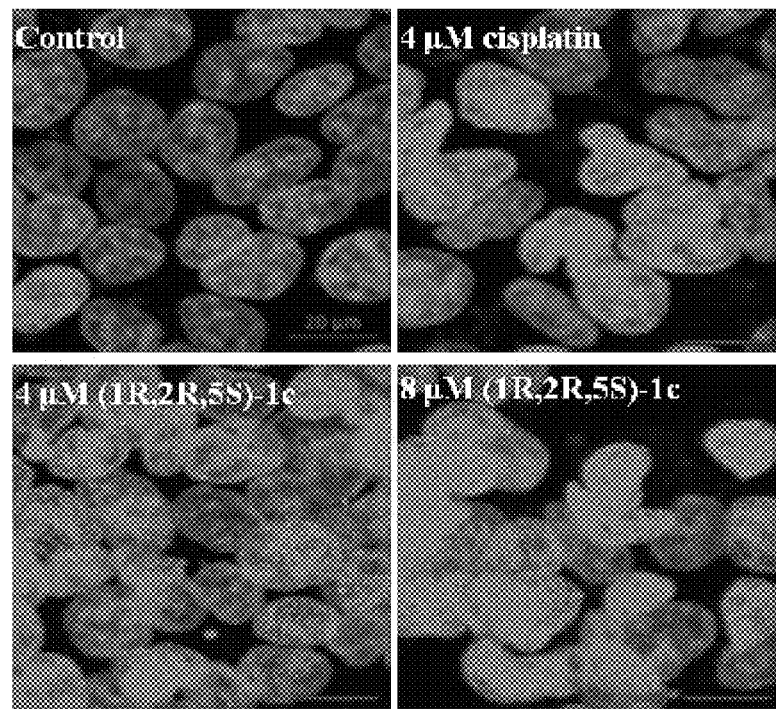

FIG. 6A graphically demonstrates (1R,2R,5S)-1c causes DNA damage in MCF-7 cells as shown by immunostaining the cells using anti-γ-H2AX IgG.

Figure 6B:
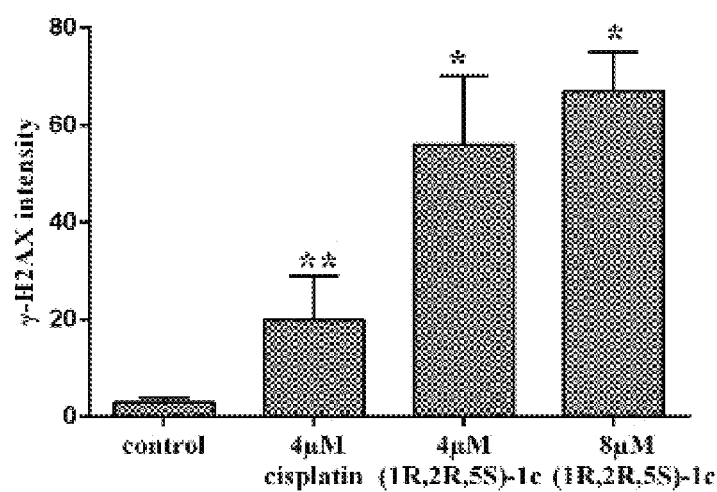

FIG. 6B graphically demonstrates γ-H2AX intensity in MCF-7 cells after treatment with (1R,2R,55)-1c.

Figure 7A:
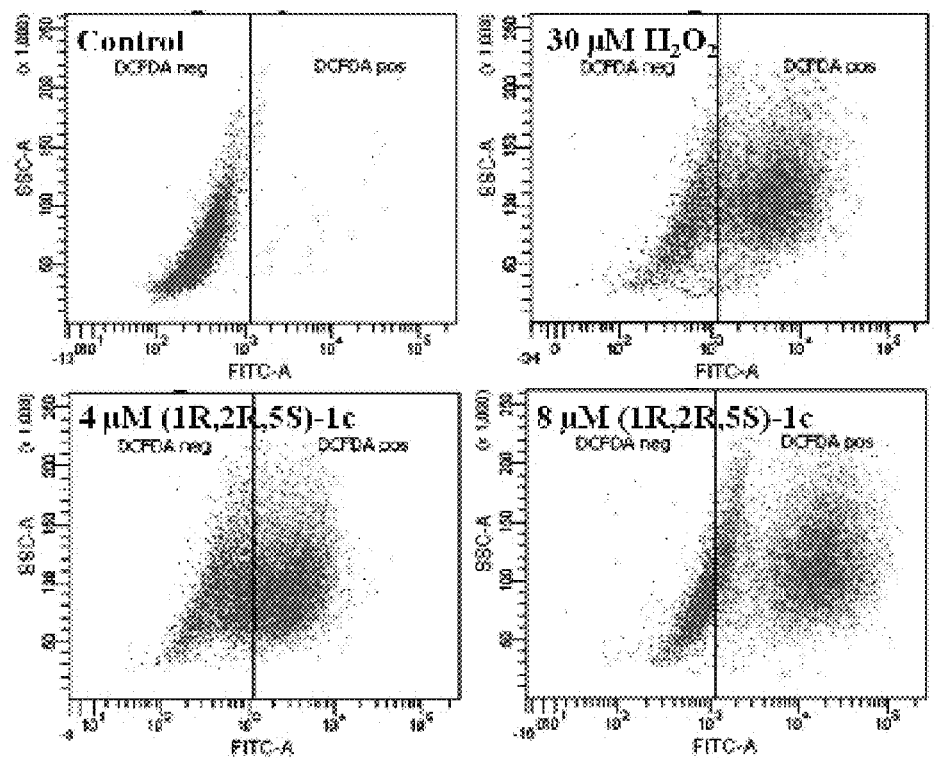

FIG. 7A graphically demonstrates intracellular ROS generation using dichlorofluoroscein-diacetate (DCFH-DA) assay in MCF-7 cells treated with media alone (negative control), 30 μM $H_2O_2$ (positive control), 4 and 8 μM (1R,2R,5S)-1c.

Figure 7B:
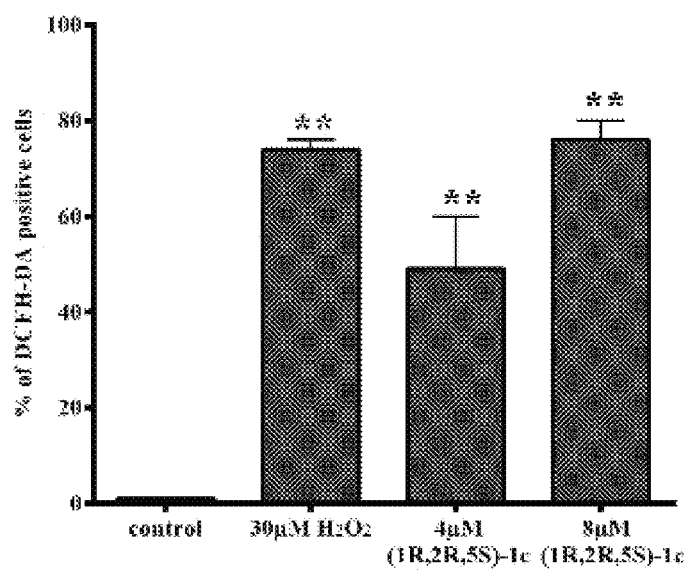

FIG. 7B graphically demonstrates % of DCFH-DA positive cells when treated with media alone (negative control), 30 μM $H_2O_2$ (positive control), 4 and 8 μM (1R,2R,5S)-1c for 24 h.

Figure 8A:
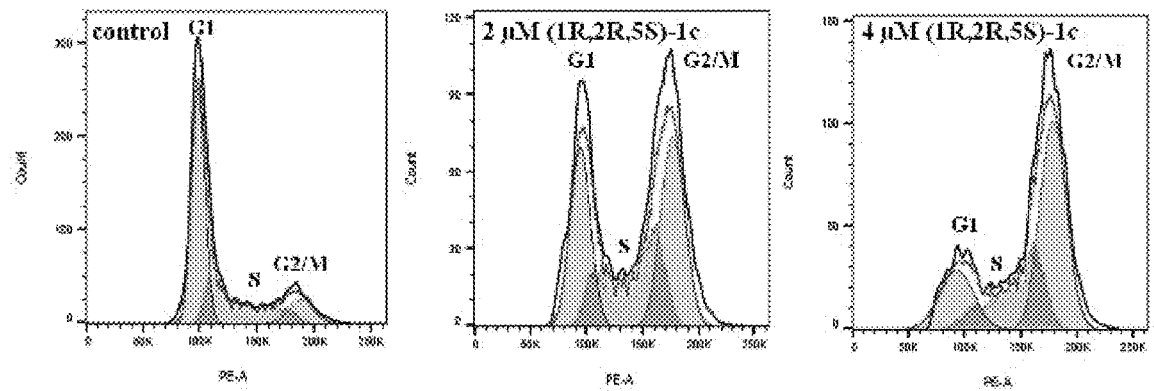

FIG. 8A graphically demonstrates (1R,2R,5S)-1c blocked cells at the G2/M phase of the cell cycle by DNA distribution profiles in different phases of the cell cycle in MCF-7 after 36 h treatment with media alone (control) or 2 and 4 μM of (1R,2R,5S)-1c.

Figure 8B:

FIG. 8B graphically demonstrates (1R,2R,5S)-1c did not arrest cells at mitosis as visualized based on DNA morphology after staining the MCF-7 cells with Hoechst 33258.

Figure 8C:
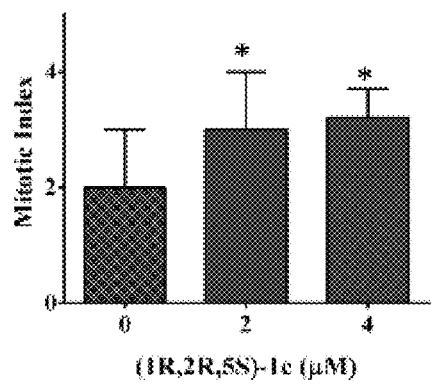

FIG. 8C graphically demonstrates the percentage of cells in mitosis (Mitotic Index).

Figure 9A:
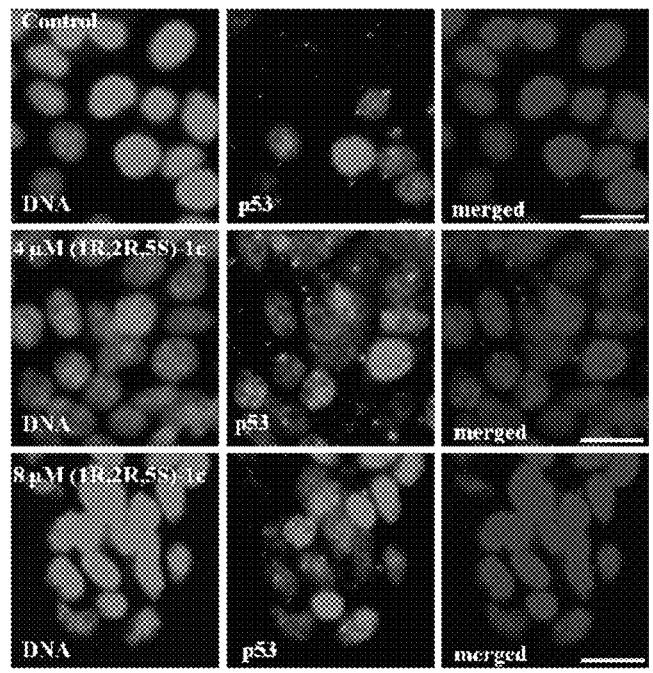

FIG. 9A graphically demonstrates (1R,2R,5S)-1c treatment leads to nuclear accumulation of p53. The left panel shows DNA of the MCF-7 cells stained with Hoechst 33258 (blue), the middle panel shows corresponding cells stained with anti-p53 IgG (red) and the right panel shows the merged image.

Figure 9B:
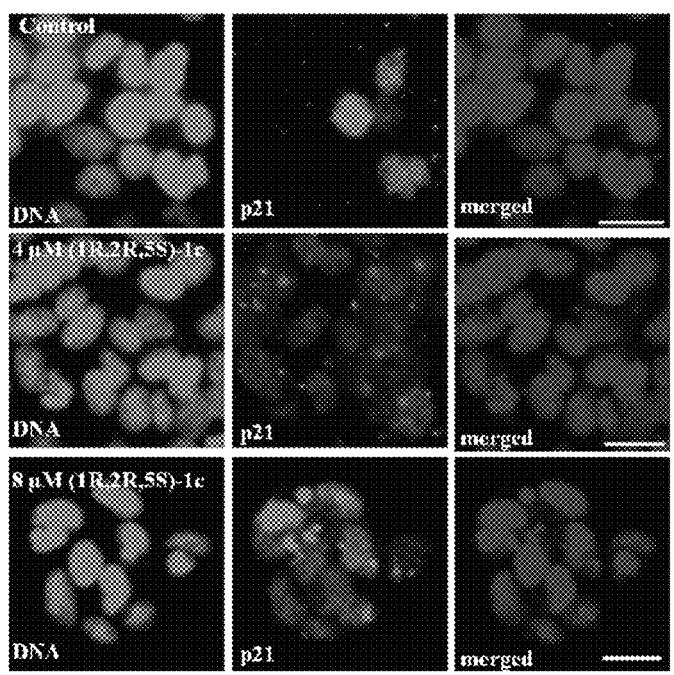

FIG. 9B graphically demonstrates (1R,2R,5S)-1c leads to nuclear accumulation of p53 which in turn transcriptionally activates p21, the downstream target of the p53 gene. The left panel shows DNA of the MCF-7 cells stained with Hoechst 33258 (blue), the middle panel shows corresponding cells stained with anti-p21 IgG (red) and the right panel shows the merged image.

DETAILED DESCRIPTION OF THE INVENTION

The following description with reference to the accompanying drawings is provided to assist in a comprehensive understanding of exemplary embodiments of the invention. It includes various specific details to assist in that understanding but these are to be regarded as merely exemplary. Accordingly, those of ordinary skill in the art will recognize that various changes and modifications of the embodiments described herein can be made without departing from the scope of the invention. In addition, descriptions of well-known functions and constructions are omitted for clarity and conciseness.

The terms and words used in the following description and claims are not limited to the bibliographical meanings, but, are merely used by the inventor to enable a clear and consistent understanding of the invention. Accordingly, it should be apparent to those skilled in the art that the following description of exemplary embodiments of the present invention are provided for illustration purpose only and not for the purpose of limiting the invention as defined by the appended claims and their equivalents.

It is to be understood that the singular forms "a," "an," and "the" include plural referents unless the context clearly dictates otherwise.

Features that are described and/or illustrated with respect to one embodiment may be used in the same way or in a similar way in one or more other embodiments and/or in combination with or instead of the features of the other embodiments.

It should be emphasized that the term "comprises/comprising" when used in this specification is taken to specify the presence of stated features, integers, steps or components but does not preclude the presence or addition of one or more other features, integers, steps, components or groups thereof.

Compounds of this invention can exist as one or more stereoisomer. The various stereoisomers include enantiomers, diastereomers and geometric isomers. Accordingly, the present invention comprises mixtures, individual stereoisomers, and optically active mixtures of compounds of Formulae (I).

The term 'NHC' as used herein refers to N-heterocyclic carbene ligands, accordingly the term Pd—NHC as used herein refers to palladium N-heterocyclic carbene complexes. The term "alkyl" as used herein includes straight-chain or branched alkyl, such as, methyl, ethyl, n-propyl, i-propyl, or the different butyl, pentyl, hexyl, heptyl, octyl, nonyl, or decyl isomers.

The term "monoanionic ligand" as used herein, includes bromide and trifluoroacetate. The term "allyl moiety", as used herein, refers to an aliphatic or aromatic substitution having at least one allyl group (i.e. —$CH_2$—CH=$CH_2$).

The term "hydrocarbyl" as used herein includes organic substituents primarily composed of carbon and hydrogen which may be aliphatic, alicyclic, aromatic or combinations thereof, e.g., aralkyl or alkaryl. Such hydrocarbyl groups may also contain aliphatic unsaturation, i.e., olefinic or acetylenic unsaturation.

The term "aryl/aromatic ring system" as used herein includes phenyl which may be optionally substituted by up to five substituents. Suitable substituents include halogen, ($C_{1-6}$)alkyl, aryl($C_{1-6}$)alkyl, ($C_{1-6}$)alkoxy, ($C_{1-6}$)alkoxy ($C_{1-6}$)alkyl, halo($C_{1-6}$)alkyl, hydroxy, nitro, amino, carboxy, carboxy salts, carboxy esters, carbamoyl, ($C_{1-6}$)alkoxycarbonyl, heterocyclyl and heterocyclyl($C_{1-6}$)alkyl. In addition, the term "aryl" may also include single and fused rings, of which at least one is aromatic, which rings may be unsubstituted or substituted by, for example, up to three substituents as set out above.

The term "heterocyclyl ring system" as used herein includes any monocyclic or polycyclic aromatic or aliphatic ring system ring system having one or more heteroatoms such as, but not limited to, nitrogen, oxygen, or sulphur. The total number of carbon atoms in a substituent group is designated by a range of "C1-C10" indicating carbon numbers from 1 to 10. For example, C1-C3 alkyl designates methyl through propyl, and C4 alkyl designates the various isomers of an alkyl group containing a total of 4 carbon atoms.

The term "$PdX_2$ or $MX_2$" broadly means $PdCl_2$, $PdBr_2$, $PdI_2$, $Pd(OCOCH_3)_2$ and $Pd(OCOCF_3)_2$.

The term "salt metathesis reaction" broadly refers to a chemical reaction involving the exchange of ions/bonds between two reacting chemical compounds, which results in the formation of products with similar or identical bonding connections.

The term "M'nYn salts" as used herein refers to AgOCOCF_3, LiOCOCF_3, NaOCOCF_3, KOCOCF_3 or NH_4OCOCF_3.

The term "cancer cell" as used herein is MCF-7, HeLa, A549, B16-F10 and EMT6/AR1.

The term "chiral hydrocarbyl" as used herein includes (1S) menthyl, (1R) menthyl, (1S,2S,5R) 2-i-propyl-5-methylcyclohexyl, (1R,2R,5S) 2-i-propyl-5-methylcyclohexyl, (1S)-pinane and (1R)-isobornyl.

The processes of the present invention and methods for the preparation of enantiomeric pairs of compounds of formula (I) via a reaction between an azolium halide salt $MX_2$ (wherein, M is Pd, X is a monoanionic ligand) followed by a salt metathesis reaction with M'nYn salt (wherein, M' is any metal, Y is any anionic ligand, n is 1 or 2) are described below. One skilled in the art will recognize that the order of addition of reagents is important in the processes of this invention.

Important are the compounds their enantiomeric forms or methods or schemes or processes described below, wherein, M is palladium (Pd); X is a monoanionic ligand selected from Br or $OCOCF_3$;

R1 is substituted or unsubstituted chiral hydrocarbyl selected from (1S) menthyl, (1R) menthyl, (1S,2S,5R) 2-i-propyl-5-methylcyclohexyl, (1R,2R,5S) 2-i-propyl-5-methylcyclohexyl, (1S)-pinane and (1R)-isobornyl.

R2 is selected from a group consisting of C1-C10 alkyl, allyl, aryl, heterocyclyl, alkylheterocyclyl; Y or Z is N, CH or $CH_2$, with the proviso that any one of Y and Z is always N.

The present invention provides a chiral palladium N-heterocyclic carbene (Pd—NHC) complexes of type $(NHC)_2PdX_2$ (wherein X is a monoanionic ligands) for exhibiting higher anticancer activities under in-vitro conditions.

An embodiment of the present invention provides a palladium N-heterocyclic carbene (Pd—NHC) metal complex of general formula (I):

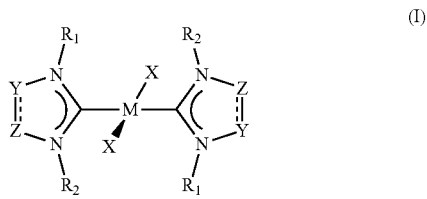

In accordance with the present invention, in the anticancer agent of above formula (I), the transition metal (M) is palladium (Pd). The substituents (R1) is chosen from optically active moieties like (1S)-menthyl, (1S,2S,5R)-2-i-propyl-5-methylcyclohexyl and (1R)-menthyl, (1R,2R,5S)-2-i-propyl-5-methylcyclohexyl (1S)-pinane and (1R)-isobornyl; whereas, R2 is preferably selected from alkyl like ethyl (Et), allyl or alkylaryl such as $CH_2Ph$. The monoanionic ligand 'X' is preferably chosen from either Br or trifluoroacetate ($OCOCF_3$); and the heteroatoms Y or Z is N or CH or $CH_2$, with the proviso that any one of Y and Z is always N.

The present inventors have further studied the influence of chirality on the anticancer properties of enantiomeric pairs of $(NHC)_2MX_2$ (wherein, M is Pd, X is Br or $OCOCF_3$) type chiral metal complexes of general formula (I) above, along with enhancement of the anticancer properties of these palladium N-heterocyclic carbene (Pd—NHC) complexes achieved through incorporation of polar functionality within the metal complexes.

Representative examples of the present chiral palladium N-heterocyclic carbene complex are:

(i) trans-[1-(1S)-menthyl-4-(ethyl)-1,2,4-triazol-5-ylidene]2PdBr_2 having formula (Ia):

Formula (Ia)

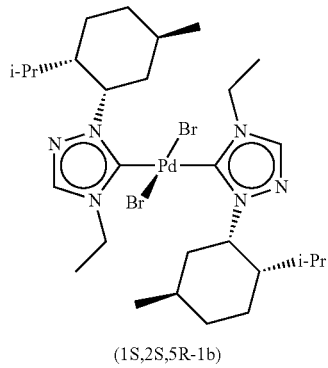

(1S,2S,5R-1b)

(ii) trans-[1-(1R)-menthyl-4-(ethyl)-1,2,4-triazol-5-ylidene]_2PdBr_2 having formula (Ib):

Formula (Ib)

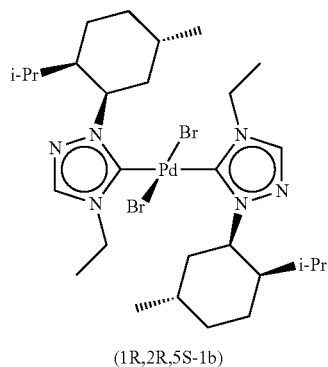

(1R,2R,5S-1b)

(iii) trans-[1-(1S)-menthyl-4-(allyl)-1,2,4-triazol-5-ylidene]$_2$PdBr$_2$ having formula (Ic):

Formula (Ic)

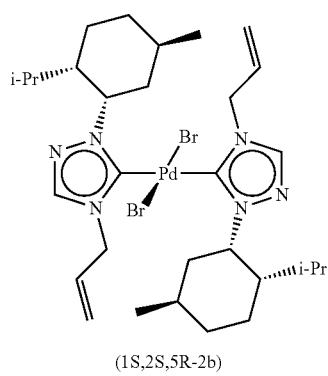

(1S,2S,5R-2b)

(iv) trans-[1-(1R)-menthyl-4-(allyl)-1,2,4-triazol-5-ylidene]$_2$PdBr$_2$ having formula (Id):

Formula (Id)

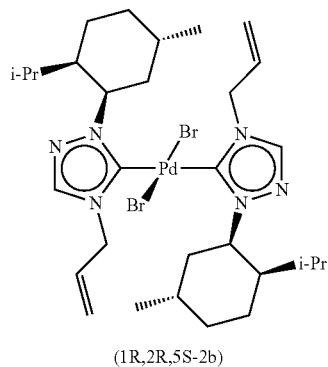

(1R,2R,5S-2b)

(v) trans-[1-(1S)-menthyl-4-(benzyl)-1,2,4-triazol-5-ylidene]2PdBr$_2$ having formula (Ie):

Formula (Ie)

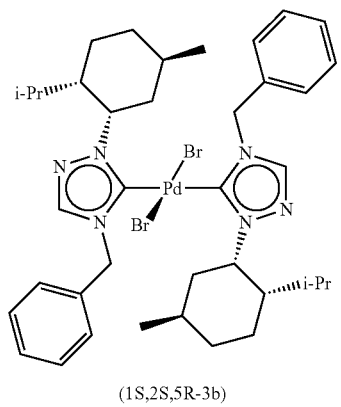

(1S,2S,5R-3b)

(vi) trans-[1-(1R)-menthyl-4-(benzyl)-1,2,4-triazol-5-ylidene]2PdBr$_2$ having formula (If):

Formula (If)

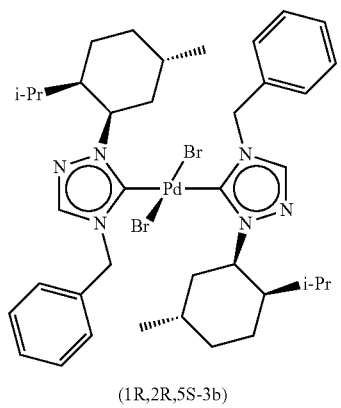

(1R,2R,5S-3b)

(vii) trans-[1-(1S)-menthyl-4-(ethyl)-1,2,4-triazol-5-ylidene]2Pd(OCOCF$_3$)$_2$ having a formula (Ig):

Formula (Ig)

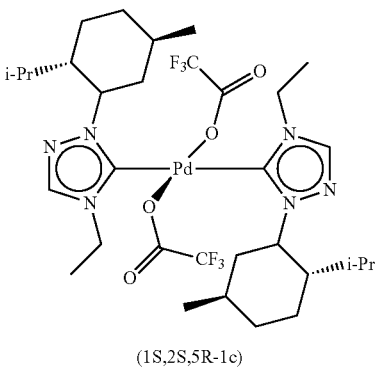

(1S,2S,5R-1c)

(viii) trans-[1-(1R)-menthyl-4-(ethyl)-1,2,4-triazol-5-ylidene]2Pd(OCOCF$_3$)$_2$ having a formula (Ih):

Formula (Ih)

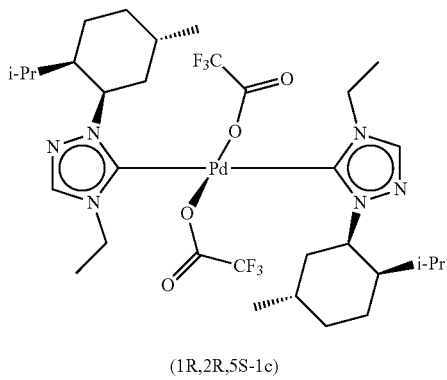

(1R,2R,5S-1c)

(ix) trans-[1-(1S)-menthyl-4-(benzyl)-1,2,4-triazol-5-ylidene]2Pd(OCOCF$_3$)$_2$ having a formula (Ii):

Formula (Ii)

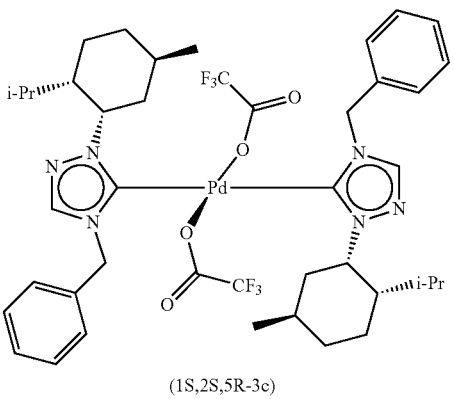

(1S,2S,5R-3c)

(x) trans-[1-(1R)-menthyl-4-(benzyl)-1,2,4-triazol-5-ylidene]2Pd(OCOCF$_3$)$_2$ having a formula (Ij):

Formula (Ij)

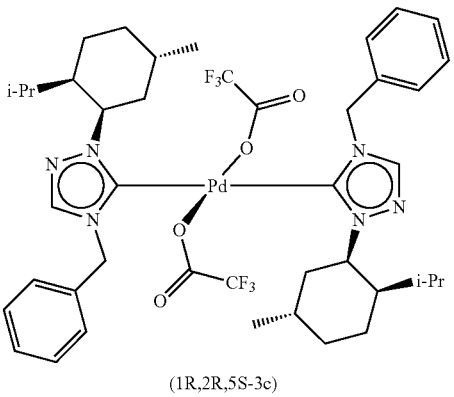

(1R,2R,5S-3c)

The present invention thus provides the compounds of formula (Ia, Ib, Ic, Id, Ie, If, Ig, Ih, Ii, and Ij) as mentioned above, which are found to be effective against the human cancer cell lines selected from MCF-7, Hela, A549, B16-F10 and EMT6/AR1.

In a preferred embodiment, the present invention provides a palladium N-heterocyclic carbene (Pd—NHC) metal complex of general formula (Ih): (1R,2R,5S)-1c Formula (Ih)

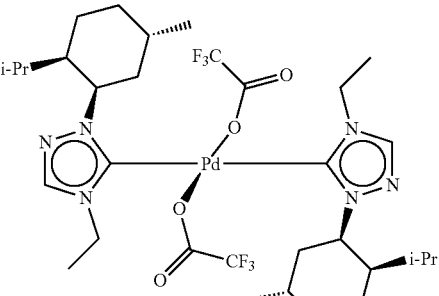

(1R,2R,5S-1c)

The present invention thus provides the compound of formula (Ih) as mentioned above, which are found to be effective against the cancer cell lines MCF-7, HeLa, B16-F10, A549 and EMT6/AR1.

Another embodiment the present invention provides a process for preparing the enantiomeric pairs of the (NHC)$_2$MX$_2$ (wherein M is Pd; X is a monoanionic ligand selected from Br or OCOCF$_3$) type of chiral complexes of general formula (I), the said process comprising of steps: (a) converting a chiral alcohol using a tosylating agent so as to make a leaving group; followed by a (b) nucleophilic substitution reaction of the tosylated chiral hydrocarbyl (R1-OTs) formed in step 'a' with a heterocyclic compound by a suitable base; (c) N-alkylation of the compound formed in step 'b' with selective alkyl halides (R2-X) to give respective azolium salts; (d) directly reacting the formed azolium salts with a metallic salt MX$_2$ (wherein, M is Pd, X is a monoanionic ligand selected from Br, Cl, I or OCOCH$_3$), in presence of a suitable base at temperature under reflux conditions forming the present (NHC)$_2$MX$_2$ type chiral precursors; followed by (e) a metal salt metathesis reaction of said (NHC)$_2$MX$_2$ type chiral precursors (wherein, M is Pd, X is selected from Br, Cl, I or OCOCH$_3$), with M'nYn, (wherein M' is any metal, Y is any anionic ligand preferably OCOCF$_3$, n is 1 or 2), under stirring in room temperature to give the final product. The said process is represented by the following general scheme 1:

Scheme 1.

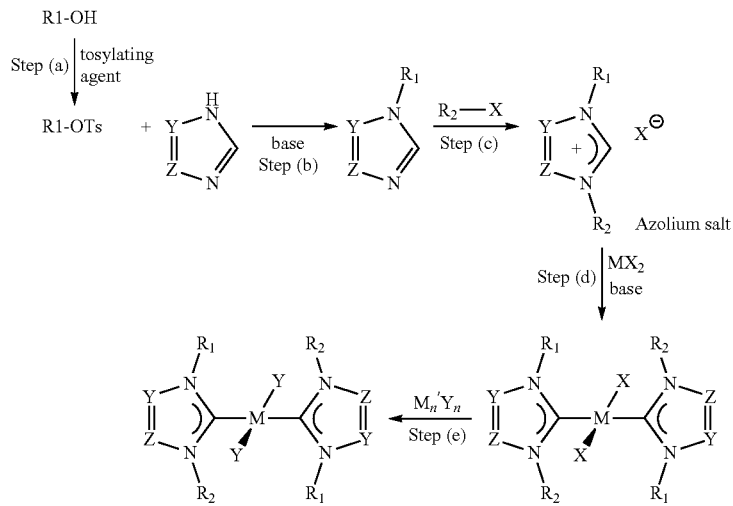

In accordance with above process of the present invention, the leaving group tosylating agent used in step (a) is for example tosyl chloride and in an amount ranging between 12.20 g and 13.20 g. Leaving group may also include trifluoromethane sulfonate ($CF_3SO_3$), para-toluene sulfonate, tosylate (OTs), methane sulfonate, mesylate (Ms), para-nitrophenyl sulfonate, nosylate (Ns), para-bromophenyl sulfonate, brosylate (Bs), carboxylate (OCOR) or phenoxides (OAr). The chiral hydrocarbyl is chosen from a group consisting of (1S) menthyl, (1R) menthyl, (1S,2S,5R) 2-i-propyl-5-methylcyclohexyl, (1R,2R,5S) 2-i-propyl-5-methylcyclohexyl, (1S)-pinane and (1R)-isobornyl; and in an amount ranging between 10.00 g and 10.50 g.

The heterocyclic compound used during the nucleophilic substitution reaction of step (b) is any heterocycle comprising of 1-3 N-heteroatoms like 1,2,4-triazole, 1,2,3-triazole, tetrazole, preferably a 1H-1,2,4-triazole in an amount ranging between 3.52 g and 5.00 g; and the base is selected from triethyl amine $Et_3N$, NaH, KOtBu, $K_2CO_3$ and $Na_2CO_3$.

The above process for preparing the current series of Pd—NHC complex is accomplished by using various alkyl halides (R2-X) in the N-alkylation step (c) which may be chosen from ethyl bromide, allyl bromide or benzyl bromide and in an amount ranging between 0.38 g and 3.18 g.

The metal salt M'nYn for salt metathesis reaction of step (e) may include $AgOCOCF_3$, $LiOCOCF_3$, $NaOCOCF_3$, $KOCOCF_3$ or $NH_4OCOCF_3$ and is used in an amount ranging between 0.09 g and 0.18 g.

Therefore, the present chiral Pd—NHC compounds of formula (Ia to Ij) are prepared by the above process of scheme 1 and their respective enantiomers are synthesized by using the optical isomer of the same starting materials and then following the above said sequential procedure.

In a preferred embodiment, the present invention provides a process for preparing a palladium N-heterocyclic carbene (Pd—NHC) metal complex of general formula (Ih): (1R, 2R,5S)-1c.

Another embodiment of the present invention provides a pharmaceutical composition comprising at least one or more chiral N-heterocyclic carbene complex of general formula (I), along with a pharmaceutically acceptable excipient.

The representative examples of Pd—NHC compounds in present pharmaceutical composition are chosen from one or more of:

(i) trans-[1-(1S)-menthyl-4-(ethyl)-1,2,4-triazol-5-ylidene]$_2$PdBr$_2$;
(ii) trans-[1-(1R)-menthyl-4-(ethyl)-1,2,4-triazol-5-ylidene]$_2$PdBr$_2$;
(iii) trans-[1-(1S)-menthyl-4-(allyl)-1,2,4-triazol-5-ylidene]$_2$PdBr$_2$;
(iv) trans-[1-(1R)-menthyl-4-(allyl)-1,2,4-triazol-5-ylidene]$_2$PdBr$_2$;
(v) trans-[1-(1S)-menthyl-4-(benzyl)-1,2,4-triazol-5-ylidene]2PdBr$_2$;
(vi) trans-[1-(1R)-menthyl-4-(benzyl)-1,2,4-triazol-5-ylidene]$_2$PdBr$_2$;
(vii) trans-[1-(1S)-menthyl-4-(ethyl)-1,2,4-triazol-5-ylidene]2Pd(OCOCF$_3$)$_2$;
(viii) trans-[1-(1R)-menthyl-4-(ethyl)-1,2,4-triazol-5-ylidene]2Pd(OCOCF$_3$)$_2$;
(ix) trans-[1-(1S)-menthyl-4-(benzyl)-1,2,4-triazol-5-ylidene]2Pd(OCOCF$_3$)$_2$;
(x) trans-[1-(1R)-menthyl-4-(benzyl)-1,2,4-triazol-5-ylidene]2Pd(OCOCF$_3$)$_2$ Thus the present invention provides a pharmaceutical composition comprising one or more of Pd—NHC compounds (i) to (x) above which are useful for treatment of breast cancer, cervical cancer, lung cancer, skin cancer and multidrug resistant cancer.

In a preferred embodiment, the present invention provides a pharmaceutical composition comprising a palladium N-heterocyclic carbene (Pd—NHC) metal complex of general formula (Ih): (1R,2R,5S)-1c, along with a pharmaceutically acceptable excipient.

The present invention provides a pharmaceutical composition comprising Pd—NHC compound, (NHC)$_2$Pd (OCOCF$_3$)$_2$ (NHC=1-(1R,2R,5S)-menthyl-4-(ethyl)-1,2,4-triazol-5-ylidene of general formula (I(h)) which is useful for treatment of breast cancer, cervical cancer, skin cancer, lung cancer and multidrug resistant cancer.

The present invention further provides a Sulforhodamine B assay method for investigating the anti-cancer efficacies of the compounds of the present Pd—NHC series on MCF-7, HeLa, A549, B16-F10 and EMT6/AR1 cancer cell lines and also for a comparative study on normal skin cell line L929 and normal epithelial breast cells MCF10A. The said Sulforhodamine B assay is conducted as per reported method (Skehan et al., J. Natl. Cancer Inst. 1990, 82, 1107). Further their potencies are compared and found to be significantly higher to that of the standard drug Cisplatin.

These series of palladium N-heterocyclic carbene complexes (formula Ia-Ij) of the present invention are found to exhibit high cytotoxic activity against MCF-7 cancer cell lines with the $IC_{50}$ value ranging between 530 nM and 705 nM; and against Hela cancer cell lines with the $IC_{50}$ value ranging between 1 µM and 4.2 µM. Furthermore, in a comparable in vitro study performed in the present invention, the potent compounds of the current chiral Pd—NHC series showed at least 27 times lesser $IC_{50}$ value against MCF-7 cell lines and at least 4 times lesser $IC_{50}$ value against HeLa cell lines in comparison to those obtained for the standard drug Cisplatin. Thus the present chiral Pd—NHC compounds demonstrates enhanced anti-cancer efficacy than standard drug Cisplatin.

The most potent compound in the series (1R,2R,5S)-1c [formula I(h)] is further tested against lung cancer cells (A549) and skin cancer cell (B16-F10) and found to exhibit high cytotoxic activity against A549 cancer cell lines with the $IC_{50}$ value ranging between 4.1 µM and 7.3 µM; and against B16-F10 cancer cell lines with the $IC_{50}$ value ranging between 0.9 µM and 1.7 µM.

Furthermore, the chiral palladium N-heterocyclic carbene complex (formula Ih) of the present invention is found to exhibit strong cytotoxic activity against the multidrug resistant cancer cell lines EMT6/AR1 with the $IC_{50}$ value ranging between 4.5 µM and 5.1 µM.

Further, in order to check the selectivity of the present compounds between the normal and cancer cells, the most potent compound in the series (1R,2R,5S)-1c [formula I(h)] is tested against skin cancer cell (B16-F10) and the normal skin cell (L929) and found to exhibit cytotoxic activity against B16-F10 cancer cell lines with the $IC_{50}$ value ranging between 0.9 µM and 1.7 µM and for the L929 normal skin cell lines with the $IC_{50}$ value ranging between 10.3 µM and 10.7 µM which is around 8.1 times more selective towards the cancer cells.

Further, in order to check the selectivity of the present compound between the normal and cancer cells, the most potent compound (1R,2R,5S)-1c (formula I(h)) is tested against breast cancer cells (MCF-7) and the normal epithelial breast cells (MCF10A) and found to exhibit cytotoxic activity against MCF-7 cancer cell lines with the $IC_{50}$ value ranging between 0.53 µM and 0.57 µM and for the MCF10A normal epithelial breast cell lines with the $IC_{50}$ value ranging between 7.7 µM and 9.5 µM which is around 16 times more selective towards the cancer cells.

Further, in order to get better understanding of the mode of action of the chiral palladium N-heterocyclic carbene complex of the formulation $(NHC)_2Pd(OCOCF_3)_2$ (NHC=1-(1R,2R,5S)-menthyl-4-(ethyl)-1,2,4-triazol-5-ylidene, and represented by Formula (Ih) is tested in PARP cleavage and is elucidated by western blot analysis using anti-PARP antibody and is compared with the standard drug cisplatin. Interestingly, the effect of Formula (Ih), (1R,2R,5S)-1c was more pronounced than cisplatin and much lower concentration of Formula (Ih), (1R,2R,5S)-1c was required to kill cells as compared to cisplatin.

Further, in order to get mechanistic insight of the chiral palladium N-heterocyclic carbene complex of the formulation $(NHC)_2Pd(OCOCF_3)_2$ (NHC=1-(1R,2R,5S)-5 menthyl-4-(ethyl)-1,2,4-triazol-5-ylidene, and represented by Formula (Ih) is tested in DNA damage by assessing the response of histone-2AX (H2AX) phosphorylation (γ-H2AX) using immunofluorescence microscopy, which showed strong DNA damaging effects on MCF-7 cells and is compared with the standard drug cisplatin. The results suggested that Formula (Ih) (1R,2R,5S)-1c had a stronger DNA damaging effect on MCF-7 cells than cisplatin.

Further, in order to get mechanistic insight of the chiral palladium N-heterocyclic carbene complex of the formulation $(NHC)_2Pd(OCOCF_3)_2$ (NHC=1-(1R,2R,5S)-menthyl-4-(ethyl)-1,2,4-triazol-5-ylidene, and represented by Formula (Ih) is tested in the generation of intracellular reactive oxygen species (ROS) and is evaluated by ROS assay using H2DCFDA in MCF-7 cells. The data suggested that DNA damage induced by formula (Ih), (1R,2R,5S)-1c leads ROS production in cells causing apoptosis following mitochondrial pathway.

Further, in order to know the effect of the Pd—NHC complex on the progression of the cell cycle and to know at what stage of the cell proliferation stops, the chiral palladium N-heterocyclic carbene complex of the formulation $(NHC)_2Pd(OCOCF_3)_2$ (NHC=1-(1R,2R,5S)-menthyl-4-(ethyl)-1,2,4-triazol-5-ylidene, and represented by Formula (Ih) is tested in the DNA distribution profiles of different phases of cell cycle and showed that Formula (Ih), (1R,2R,5S)-1c blocks MCF-7 cells at the G2 phase and prevented the cells from entering into mitosis, which subsequently induced apoptosis in these cells. Further, in order to get better understanding of the mode of action of the chiral palladium N-heterocyclic carbene complex of the formulation $(NHC)_2Pd(OCOCF_3)_2$ (NHC=1-(1R,2R,5S)-menthyl-4-(ethyl)-1,2,4-triazol-5-ylidene, and represented by Formula (Ih) is tested in the p53 pathway, to ensure that apoptosis follows the G2 arrest. The data suggested that nuclear accumulation of p53 resulted in the activation of p53-responsive genes and subsequent apoptosis in cells. The results indicated that DNA damage induced by Formula (Ih), (1R,2R,5S)-1c arrested cells at the G2 phase of the cell cycle and followed p53-dependent pathway for cell death.

The present invention is further illustrated by following examples, which should not be constructed by way of limiting the scope of the present invention.

EXAMPLES

Example 1: Process for Preparing Compound (1S,2S,5R-1c)

Example 1 illustrates the schematic process for preparing trans-[1-(1S)-menthyl-4-(ethyl)-1,2,4-triazol-5-ylidene]2Pd $(OCOCF_3)_2$ (1S,2S,5R-1c).

The preparation of the compound trans-[1-(1S)-menthyl-4-(ethyl)-1,2,4-triazol-5-ylidene]$_2$Pd$(OCOCF_3)_2$ (1S,2S,5R-1c) involves five synthetic steps of; a) Tosylation of (1R,2S,5R)-2-i-propyl-5-methylcyclohexanol using the tosylating reagent 4-toluenesulfonyl chloride to get the (1R,2S,5R)-2-i-propyl-5-methylcyclohexyl 4-methylbenzenesulfonate; b) Nucleophilic substitution reaction of (1R,2S,5R)-2-i-propyl-5-methylcyclohexyl 4-methylbenzenesulfonate with 1H-1,2,4-triazole facilitated by a suitable base to give 1-((2S,5R)-2-i-propyl-5-methylcyclohexyl)-1,2,4-triazole, (1S,2S,5R-A); c) N-alkylation of ((1S,2S,5R)-2-i-propyl-5-methylcyclohexyl)-1,2,4-triazole, (1S,2S,5R-A) with various alkyl bromide (R2-Br) to give the triazolium salts (1S,2S,5R)-(1-3)a; d) Metallation of the triazolium salts (1S,2S,5R)-(1-3)a with $PdX_2$ (X=anionic ligand) type palladium precursors to give the $(NHC)_2PdX_2$ type chiral complexes (1S,2S,5R)-(1-3)b; e) Salt metathesis reaction of the $(NHC)_2PdX_2$ type complexes (1S,2S,5R)-(1-3)b with $AgOCOCF_3$ to give (1S,2S,5R)-(1c & 3c). The base used in tosylation reaction is NaH for step (a) and $Et_3N$ for the metallation reaction of step (e). The schematic reaction is thus represented in Scheme 2 below:

Scheme 2.

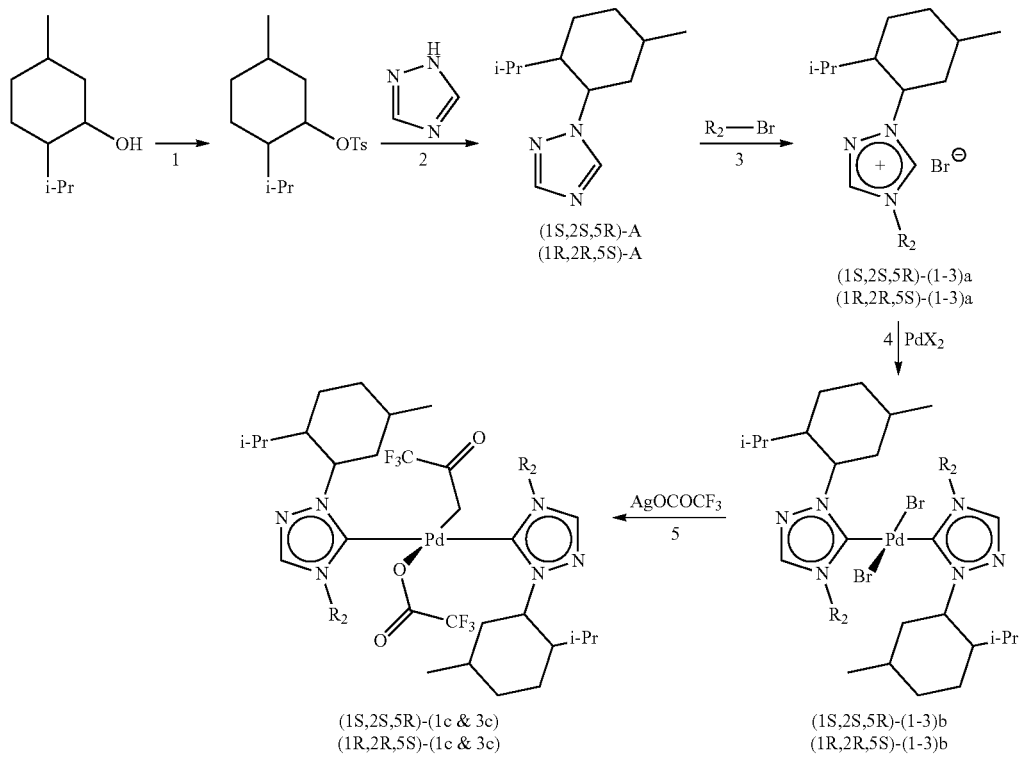

Each Step Involved in the Above Scheme 2 is Exemplified Below

Step (a, b): Synthesis of 1-(1S)-menthyl-1H-1,2,4-triazole (1S,2S,5R-A)

A 250 mL round bottom flask is charged with 1,2,4-triazole (3.52 g, 51.0 mmol), (1R,2S,5R)-2-i-propyl-5-methylcyclohexyl-4-methylbenzenesulfonate (7.00 g, 22.5 mmol) and DMF (ca. 70 mL) and to which NaH is added portion wise (2.00 g, 83.3 mmol) over 20 minutes at 0° C. and further the reaction mixture is allowed to stir at room temperature for 30 minutes then refluxed for 24 hours. Upon completion of the reaction, the reaction mixture is cooled to room temperature and EtOAc (ca. 400 mL) is added. The reaction mixture is washed with water (ca. 12×50 mL) and the organic layer is collected and vacuum dried to give crude product as a colourless liquid which is finally purified by column chromatography using silica gel as a stationary phase and eluting with a mixed medium of petroleum ether/EtOAc (90:10 v/v) to give the product 1S,2S,5R-A as a colourless solid (2.52 g, 54%).

Step (c): Synthesis of 1-(1S)-menthyl-4-(ethyl)-1,2,4-triazolium bromide (1S,2S,5R-1a)

A mixture of 1-(1S)-menthyl-1H-1,2,4-triazole (1.52 g, 7.33 mmol) (1S,2S,5R-A) and ethyl bromide (3.18 g, 29.2 mmol) is refluxed overnight in $CH_3CN$ (ca. 40 mL), and after the completion of reaction the solvent is removed under vacuum. The residue thus obtained is washed with hot $Et_2O$ (ca. 3×10 mL) and vacuum dried to give the product 1S,2S,5R-1a as a white solid (0.924 g, 40%).

Step (d): Synthesis of trans-[1-(1S)-menthyl-4-(ethyl)-1,2,4-triazol-5-ylidene]$_2$PdBr$_2$ (1S,2S,5R-1b)

A mixture of 1-(1S)-menthyl-4-(ethyl)-1,2,4-triazolium bromide (0.474 g, 1.50 mmol) (1S,2S,5R-1a), PdBr$_2$ (0.200 g, 0.751 mmol) and Et$_3$N (0.606 g, 5.99 mmol) in $CH_3CN$ (ca. 50 mL) is refluxed for 12 hours. The solvent is removed under vacuum to obtain the crude product and is finally purified by column chromatography using silica gel as a stationary phase and eluting with a mixed medium of petroleum ether/EtOAc (85:15 v/v) to give the product 1S,2S,5R-1b as a light yellow solid (0.519 g, 94%). The said compound 1S,2S,5R-1b having formula (Ia) below:

Formula (Ia)

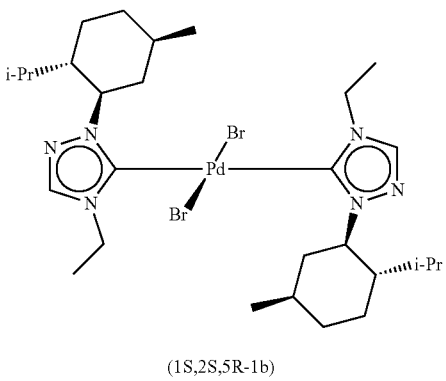

(1S,2S,5R-1b)

Yield: 94%
Spectral data:
$^1$H NMR (CDCl$_3$, 400 MHz, 25° C.): (Major) δ 7.87 (s, 2H, N—C(3)H—N), 5.70 (br, 2H, CH$_3$C$_6$H$_9$CH(CH$_3$)$_2$), 4.78 (qd, 2H, $^3J_{HH}$=7 Hz, C$\underline{H}$2CH$_3$), 4.46 (qd, 2H, $^3J_{HH}$=7 Hz, C$\underline{H}$2CH$_3$), 2.59-1.00 (m, 18H, CH$_3$C$_6$$\underline{H}$$_9$CH(CH$_3$)$_2$ & CH$_3$C$_6$H$_9$C$\underline{H}$(CH$_3$)$_2$), 1.73 (t, 6H, $^3J_{HH}$=7 Hz, CH$_2$C$\underline{H}$$_3$), 1.12 (d, 6H, $^3J_{HH}$=7 Hz, CH$_3$C$_6$H$_9$CH(C$\underline{H}$$_3$)$_2$), 0.85 (d, 6H, $^3J_{HH}$=7 Hz, CH$_3$C$_6$H$_9$CH(C$\underline{H}$$_3$)$_2$), 0.74 (d, 6H, $^3J_{HH}$=7 Hz, C$\underline{H}$$_3$C$_6$H$_9$CH(CH$_3$)$_2$). (Minor) δ 7.87 (s, 1H, N—C(3)$\underline{H}$—N), 5.61 (br, 2H, CH$_3$C$_6$$\underline{H}$$_9$CH(CH$_3$)$_2$), 4.74 (qd, 2H, $^3J_{HH}$=7 Hz, C$\underline{H}$$_2$CH$_3$), 4.42 (qd, 2H, $^3J_{HH}$=7 Hz, C$\underline{H}$$_2$CH$_3$), 2.59-1.00 (m, 18H, CH$_3$C$_6$$\underline{H}$$_9$CH(CH$_3$)$_2$ & CH$_3$C$_6$$\underline{H}$$_9$CH(CH$_3$)$_2$), 1.71 (t, 6H, $^3J_{HH}$=7 Hz, CH$_2$C$\underline{H}$$_3$), 1.09 (d, 6H, $^3J_{HH}$=7 Hz, CH$_3$C$_6$H$_9$CH(C$\underline{H}$$_3$)$_2$), 0.84 (d, 6H, $^3J_{HH}$=7 Hz, CH$_3$C$_6$H$_9$CH(C$\underline{H}$$_3$)$_2$), 0.72 (d, 6H, $^3J_{HH}$=7 Hz, C$\underline{H}$$_3$C$_6$H$_9$CH(CH$_3$)$_2$). $^{13}$C{$^1$H}NMR (CDCl$_3$, 100 MHz, 25° C.): (Major) δ 172.2 (Pd—NCN), 140.7 (N—C(3)H—N), 60.7 (CH$_3$$\underline{C}$$_6$H$_9$CH(CH$_3$)$_2$), 47.6 (CH$_3$$\underline{C}$$_6$H$_9$CH(CH$_3$)$_2$), 44.1 ($\underline{C}$H$_2$CH$_3$), 41.6 (CH$_3$$\underline{C}$$_6$H$_9$CH(CH$_3$)$_2$), 35.5 (CH$_3$$\underline{C}$$_6$H$_9$CH(CH$_3$)$_2$), 29.1 (CH$_3$$\underline{C}$$_6$H$_9$CH(CH$_3$)$_2$), 26.2 (CH$_3$C$_6$H$_9$$\underline{C}$H(CH$_3$)$_2$), 24.3 (CH$_3$$\underline{C}$$_6$H$_9$CH(CH$_3$)$_2$), 23.3 ($\underline{C}$H$_3$C$_6$H$_9$CH(CH$_3$)$_2$), 22.6 (CH$_3$C$_6$H$_9$CH($\underline{C}$H$_3$)$_2$), 20.3 (CH$_3$C$_6$H$_9$CH($\underline{C}$H$_3$)$_2$), 16.1 (CH$_2$$\underline{C}$H$_3$). (Minor) δ 172.1 (Pd—NCN), 140.5 (N—$\underline{C}$(3)H—N), 60.7 (CH$_3$$\underline{C}$$_6$H$_9$CH(CH$_3$)$_2$), 47.5 (CH$_3$$\underline{C}$$_6$H$_9$CH(CH$_3$)$_2$), 44.1 ($\underline{C}$H$_2$CH$_3$), 41.3 (CH$_3$$\underline{C}$$_6$H$_9$CH(CH$_3$)$_2$), 35.5 (CH$_3$$\underline{C}$$_6$H$_9$CH(CH$_3$)$_2$), 29.0 (CH$_3$$\underline{C}$$_6$H$_9$CH(CH$_3$)$_2$), 26.2 (CH$_3$C$_6$H$_9$$\underline{C}$H(CH$_3$)$_2$), 24.2 (CH$_3$$\underline{C}$$_6$H$_9$CH(CH$_3$)$_2$), 23.3 ($\underline{C}$H$_3$C$_6$H$_9$CH(CH$_3$)$_2$), 22.6 (CH$_3$C$_6$H$_9$$\underline{C}$H(CH$_3$)$_2$), 20.3 (CH$_3$C$_6$H$_9$CH($\underline{C}$H$_3$)$_2$), 16.0 (CH$_2$$\underline{C}$H$_3$). IR data (KBr pellet) cm$^{-1}$: 3434 (w), 3126 (m), 3055 (w), 2950 (s), 2870 (s), 1699 (w), 1540 (m), 1443 (s), 1387 (m), 1352 (w), 1283 (w), 1262 (w), 1212 (m), 1189 (w), 1140 (w), 1096 (w), 1008 (w), 981 (w), 940 (w), 872 (w), 846 (w), 801 (w), 777 (w), 659 (m). HRMS (ES): m/z 657.2304 [M-Br]$^+$, calcd. 657.2308. Anal. Calcd. for C$_{28}$H$_{50}$PdBr$_2$N$_6$: C, 45.63; H, 6.84; N, 11.40. Found: C, 45.90; H, 6.67; N, 11.39%. [α]$_D^{25}$ −29.4 (c 1.00 in CHCl$_3$).

Step (e): Synthesis of trans-[1-(1S)-menthyl-4-(ethyl)-1,2,4-triazol-5-ylidene]$_2$Pd(OCOCF$_3$)$_2$ (1S,2S,5R-1c)

To a compound of formula (1S,2S,5R-1b), trans-[1-(1S)-menthyl-4-(ethyl)-1,2,4-triazol-5-ylidene]$_2$PdBr$_2$ (0.230 g, 0.312 mmol) and AgOCOCF$_3$ (0.152 g, 0.687 mmol) are stirred in CH$_2$Cl$_2$ (ca. 20 mL) at room temperature for 4 hours. The reaction mixture was filtered over celite and solvent was removed under vacuum to obtain the crude product. The crude product was finally purified by column chromatography using silica gel as a stationary phase and eluting with a mixed medium of petroleum ether/EtOAc (80:20 v/v) to give the product 1S,2S,5R-1c as a colourless solid (0.152 g, 61%).

Example 2: Compound—trans-[1-(1S)-menthyl-4-(ethyl)-1,2,4-triazol-5-ylidene]$_2$Pd(OCOCF$_3$)$_2$ (1S,2S,5R-1c)

Example 2 illustrates the compound trans-[1-(1S)-menthyl-4-(ethyl)-1,2,4-triazol-5-ylidene]$_2$Pd(OCOCF$_3$)$_2$ (1S,2S,5R-1c), prepared by the process as described in example 1 above and having a formula (Ig) as below:

Formula (Ig)

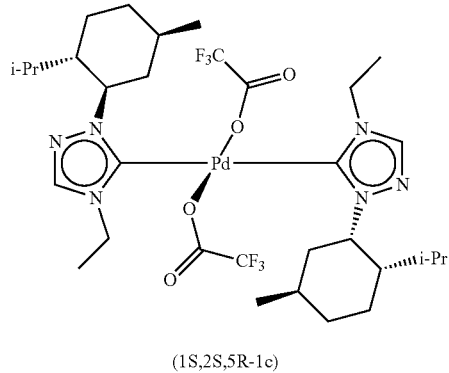

(1S,2S,5R-1c)

Yield: 61%
Spectral data:
$^1$H NMR (CDCl$_3$, 500 MHz, 25° C.): δ 7.93 (s, 2H, N—C(3)$\underline{H}$—N), 5.90 (br, 2H, CH$_3$C$_6$$\underline{H}$$_9$CH(CH$_3$)$_2$), 4.78 (br, 4H, C$\underline{H}$$_2$CH$_3$), 2.09-0.98 (m, 18H, CH$_3$C$_6$$\underline{H}$$_9$CH(CH$_3$)$_2$ & CH$_3$C$_6$H$_9$C$\underline{H}$(CH$_3$)$_2$), 1.62 (br, 6H, CH$_2$C$\underline{H}$$_3$), 1.06 (br, 6H, CH$_3$C$_6$H$_9$CH(C$\underline{H}$$_3$)$_2$), 0.74 (d, 6H, $^3J_{HH}$=6 Hz, C$\underline{H}$$_3$C$_6$H$_9$CH(CH$_3$)$_2$), 0.74 (br, 6H, CH$_3$C$_6$H$_9$CH(C$\underline{H}$$_3$)$_2$). $^{13}$C{$^1$H}NMR (CDCl$_3$, 100 MHz, 25° C.), δ 168.1 (Pd—NCN), 162.3 (q, $^3J_{CF}$=40 Hz, O$\underline{C}$OCF$_3$), 140.6 (N—$\underline{C}$(3)H—N), 114.1 (q, $^2J_{CF}$=288 Hz, OCO$\underline{C}$F$_3$), 60.6 (CH$_3$$\underline{C}$$_6$H$_9$CH(CH$_3$)$_2$), 47.1 ($\underline{C}$H$_2$CH$_3$), 43.9 (CH$_3$$\underline{C}$$_6$H$_9$CH(CH$_3$)$_2$), 41.4 (CH$_3$$\underline{C}$$_6$H$_9$CH(CH$_3$)$_2$), 35.2 (CH$_3$$\underline{C}$$_6$H$_9$CH(CH$_3$)$_2$), 29.5 (CH$_3$$\underline{C}$$_6$H$_9$CH(CH$_3$)$_2$), 26.1 (CH$_3$C$_6$H$_9$$\underline{C}$H(CH$_3$)$_2$), 24.5 (CH$_3$$\underline{C}$$_6$H$_9$CH(CH$_3$)$_2$), 22.2 ($\underline{C}$H$_3$C$_6$H$_9$CH(CH$_3$)$_2$), 21.6 (CH$_3$C$_6$H$_9$CH($\underline{C}$H$_3$)$_2$), 20.1 (CH$_3$C$_6$H$_9$CH($\underline{C}$H$_3$)$_2$), 15.5 (CH$_2$$\underline{C}$H$_3$). $^{19}$F{$^1$H}NMR (CDCl$_3$, 470 MHz, 25° C.) δ −73.79 (Pd—OCO$\underline{C}$F$_3$). IR data (KBr pellet) cm$^{-1}$: 3125 (w), 3060 (w), 2960 (m), 2924 (w), 2873 (w), 2849 (w), 1696 (s), 1571 (w), 1542 (w), 1458 (w), 1406 (w), 1371 (w), 1262 (w), 1224 (w), 1189 (s), 1147 (m), 1096 (w), 1012 (w), 850 (w), 799 (w), 786 (w), 732 (w). HRMS (ES): m/z 689.2988 [M-OCOCF$_3$]$^+$, calcd. 689.2988. Anal. Calcd. for C$_{32}$H$_{50}$F$_6$N$_6$O$_4$Pd: C, 47.85; H, 6.27; N, 10.46. Found: C, 48.34; H, 5.96; N, 10.71%. [α]$_D^{25}$ +47.8 (c 1.00 in CHCl$_3$).

Example 3: Process for Synthesis of Compound 1S,2S,5R-2b

Example 3 illustrates the schematic process for preparing trans-[1-(1S)-menthyl-4-(allyl)-1,2,4-triazol-5-ylidene]$_2$PdBr$_2$ (1S,2S,5R-2b).

Process steps involved: —

Steps (a) is Same as Steps (a) of the Process Described in Example 1 Above

Step (b): Synthesis of 1-(1S)-menthyl-4-(allyl)-1,2,4-triazolium Bromide (1S,2S,5R-2a)

The compound of formula (1S,2S,5R-A), 1-(1S)-menthyl-1H-1,2,4-triazole (1.20 g, 5.79 mmol) is taken in CH$_3$CN (ca. 40 mL) and to which allyl bromide (2.81 g, 23.2 mmol) is added and further the reaction mixture is refluxed in for 24 hours, then the solvent is removed under vacuum. The residue thus obtained is washed with hot Et$_2$O (ca. 3×10 mL) and vacuum dried to give the product 1S,2S,5R-2a as a white solid (1.53 g, 80%).

Step (c, d): Synthesis of trans-[1-(1S)-menthyl-4-(allyl)-1,2,4-triazol-5-ylidene]$_2$PdBr$_2$ (1S,2S,5R-2b)

In a 100 mL round bottom flask, the compound of formula (1S,2S,5R-2a), 1-(1S)-menthyl-4-(allyl)-1,2,4-triazolium bromide (0.495 g, 1.51 mmol), PdBr$_2$ (0.200 g, 0.751 mmol) and Et$_3$N (0.606 g, 5.99 mmol) and CH$_3$CN (ca. 50 mL) are charged and is refluxed for 12 hours. After the completion of reaction, the solvent is removed under vacuum to obtain the crude product which is finally purified by column chromatography using silica gel as a stationary phase and eluting with a mixed medium of petroleum ether/EtOAc (88:12 v/v) to give the product 1S,2S,5R-2b as a light yellow solid (0.408 g, 71%).

Example 4: Compound—trans-[1-(1S)-menthyl-4-(allyl)-1,2,4-triazol-5-ylidene]$_2$PdBr$_2$ (1S,2S,5R-2b)

Example 4 illustrates the compound trans-[1-(1S)-menthyl-4-(allyl)-1,2,4-triazol-5-ylidene]$_2$PdBr$_2$ (1S,2S,5R-2b), prepared by the process as described in example 3 above and having a formula (Ic) as below:

Formula (Ic)

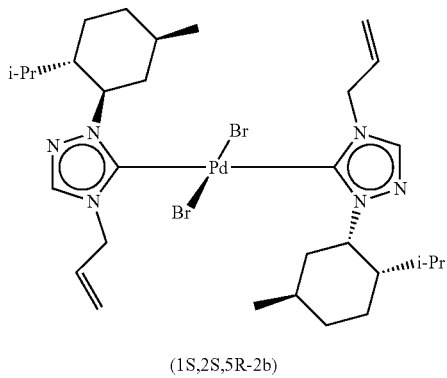

(1S,2S,5R-2b)

Yield: 71%
Spectral data:
$^1$H NMR (CDCl$_3$, 400 MHz, 25° C.): (Major) δ 7.86 (s, 2H, N—C(3)H—N), 6.24 (m, 2H, CH$_2$CH=CH$_2$), 5.73 (br, 2H, CH$_3$C$_6$H$_9$CH(CH$_3$)$_2$), 5.45 (m, 4H, CH$_2$CH=CH$_2$), 5.30 (m, 2H, CH$_2$CH=CH$_2$), 5.07 (qd, 2H, $^2J_{HH}$=15 Hz, $^3J_{HH}$=6 Hz, CH$_2$CH=CH$_2$), 2.59-0.88 (m, 18H, CH$_3$C$_6$H$_9$CH(CH$_3$)$_2$ & CH$_3$C$_6$H$_9$CH(CH$_3$)$_2$), 1.14 (d, 6H, $^3J_{HH}$=7 Hz, CH$_3$C$_6$H$_9$CH(CH$_3$)$_2$), 0.83 (d, 6H, $^3J_{HH}$=7 Hz, CH$_3$C$_6$H$_9$CH(CH$_3$)$_2$), 0.74 (d, 6H, $^3J_{HH}$=7 Hz, CH$_3$C$_6$H$_9$CH(CH$_3$)$_2$). (Minor) 7.86 (s, 2H, N—C(3)H—N), 6.24 (m, 2H, CH$_2$CH=CH$_2$), 5.72 (br, 2H, CH$_3$C$_6$H$_9$CH(CH$_3$)$_2$), 5.40 (m, 4H, CH$_2$CH=CH$_2$), 5.30 (m, 2H, CH$_2$CH=CH$_2$), 5.04 (qd, 2H, $^2J_{HH}$=15 Hz, $^3J_{HH}$=6 Hz, CH$_2$CH=CH$_2$), 2.59-0.88 (m, 18H, CH$_3$C$_6$H$_9$CH(CH$_3$)$_2$ & CH$_3$C$_6$H$_9$CH(CH$_3$)$_2$), 1.08 (d, 6H, $^3J_{HH}$=7 Hz, CH$_3$C$_6$H$_9$CH(CH$_3$)$_2$), 0.83 (d, 6H, $^3J_{HH}$=7 Hz, CH$_3$C$_6$H$_9$CH(CH$_3$)$_2$), 0.71 (d, 6H, $^3J_{HH}$=7 Hz, CH$_3$C$_6$H$_9$CH(CH$_3$)$_2$). $^{13}$C{$^1$H}NMR (CDCl$_3$, 100 MHz, 25° C.): (Major) δ 172.3 (Pd—NCN), 140.9 (N—C(3)H—N), 132.2 (CH$_2$CH=CH$_2$), 120.8 (CH$_2$CH=CH$_2$), 60.7 (CH$_3$C$_6$H$_9$CH(CH$_3$)$_2$), 51.7 (CH$_2$CH=CH$_2$), 47.6 (CH$_3$C$_6$H$_9$CH(CH$_3$)$_2$), 41.6 (CH$_3$C$_6$H$_9$CH(CH$_3$)$_2$), 35.5 (CH$_3$C$_6$H$_9$CH(CH$_3$)$_2$), 29.1 (CH$_3$C$_6$H$_9$CH(CH$_3$)$_2$), 26.2 (CH$_3$C$_6$H$_9$CH(CH$_3$)$_2$), 24.3 (CH$_3$C$_6$H$_9$CH(CH$_3$)$_2$), 23.4 (CH$_3$C$_6$H$_9$CH(CH$_3$)$_2$), 22.6 (CH$_3$C$_6$H$_9$CH(CH$_3$)$_2$), 20.3 (CH$_3$C$_6$H$_9$CH(CH$_3$)$_2$). (Minor) δ 172.3 (Pd—NCN), 140.9 (N—C(3)H—N), 132.2 CH$_2$CH=CH$_2$), 120.5 (CH$_2$CH=CH$_2$), 60.7 (CH$_3$C$_6$H$_9$CH(CH$_3$)$_2$), 51.7 (CH$_2$CH=CH$_2$), 47.5 (CH$_3$C$_6$H$_9$CH(CH$_3$)$_2$), 41.4 (CH$_3$C$_6$H$_9$CH(CH$_3$)$_2$), 35.5 (CH$_3$C$_6$H$_9$CH(CH$_3$)$_2$), 29.1 (CH$_3$C$_6$H$_9$CH(CH$_3$)$_2$), 26.2 (CH$_3$C$_6$H$_9$CH(CH$_3$)$_2$), 24.1 (CH$_3$C$_6$H$_9$CH(CH$_3$)$_2$), 23.3 (CH$_3$C$_6$H$_9$CH(CH$_3$)$_2$), 22.6 (CH$_3$C$_6$H$_9$CH(CH$_3$)$_2$), 20.3 (CH$_3$C$_6$H$_9$CH(CH$_3$)$_2$). IR data (KBr pellet) cm$^{-1}$: 3436 (m), 3123 (m), 3051 (w), 3017 (w), 2955 (s), 2867 (s), 2848 (s), 2722 (w), 1640 (w), 1538 (s), 1459 (w), 1432 (m), 1388 (w), 1369 (w), 1350 (w), 1331 (m), 1285 (w), 1245 (m), 1227 (w), 1201 (w), 1176 (m), 1139 (w), 1007 (w), 984 (m), 931 (w), 918 (m), 871 (w), 844 (w), 787 (m), 717 (w), 666 (m) 614 (w), 562 (w). HRMS (ES): m/z 681.2299 [M-Br]$^+$, calcd. 681.2308. Anal. Calcd. for C$_{30}$H$_{50}$PdBr$_2$N$_6$: C, 47.35; H, 6.62; N, 11.04. Found: C, 47.72; H, 6.56; N, 11.13%. $[\alpha]_D^{25}$ −41.7 (c 1.00 in CHCl$_3$).

Example 5: Process for Synthesis of Compound (1S,2S,5R-3c)

Example 5 illustrates the schematic process for preparing trans-[1-(1S)-menthyl-4-(benzyl)-1,2,4-triazol-5-ylidene]$_2$Pd(OCOCF$_3$)$_2$ (1S,2S,5R-3c).

Process steps involved: —

Steps (a) is Same as Steps (a) of the Process Described in Above Example 1

Step (b): Synthesis of 1-(1S)-menthyl-4-(benzyl)-1,2,4-triazolium Bromide (1S,2S,5R-3a)

To a mixture of 1-(1S)-menthyl-1H-1,2,4-triazole (1S,2S,5R-A) (0.928 g, 4.48 mmol) in CH$_3$CN (ca. 40 mL), benzyl bromide (0.766 g, 4.48 mmol) is added and refluxed for overnight, after which the solvent is removed under vacuum. The residue thus obtained is washed with hot Et$_2$O (ca. 3×10 mL) and vacuum dried to give the product 1S,2S,5R-3a as a white solid (1.42 g, 84%).

Step (c, d): Synthesis of trans-[1-(1S)-menthyl-4-(benzyl)-1,2,4-triazol-5-ylidene]$_2$PdBr$_2$ (1S,2S,5R-3b)

To a stirred solution of 1-(1S)-menthyl-4-(benzyl)-1,2,4-triazolium bromide (1S,2S,5R-3a) (0.568 g, 1.50 mmol) in CH$_3$CN (ca. 50 mL), PdBr$_2$ (0.200 g, 0.751 mmol) and Et$_3$N (0.606 g, 5.99 mmol) are added and refluxed for 12 hours. The solvent is removed under vacuum and the crude product is finally purified by column chromatography using silica gel as a stationary phase and eluting with a mixed medium of petroleum ether/EtOAc (88:12 v/v) to give the product 1S,2S,5R-3b as a light yellow solid (0.458 g, 71%). The said compound having formula (Ie) below:

Formula (Ie)

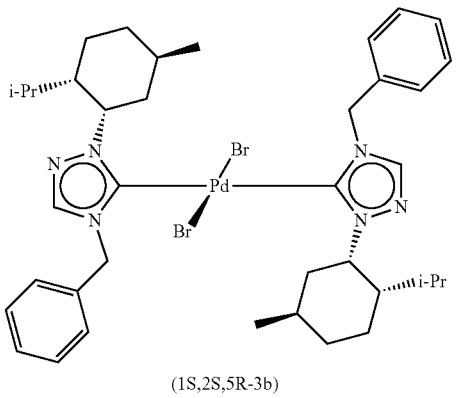

(1S,2S,5R-3b)

Yield: 71%

Spectral data:

$^1$H NMR (CDCl$_3$, 400 MHz, 25° C.): (Major) δ 7.65 (s, 1H, N—C(3)H—N), 7.53 (br, 2H, (C$_6$H$_5$), 7.45 (br, 4H, C$_6$H$_5$), 7.35 (br, 4H, C$_6$H$_5$), 5.73 (d, 2H, $^2$J$_{HH}$=15 Hz, CH$_2$), 5.67 (br, 2H, CH$_3$C$_6$H$_9$CH(CH$_3$)$_2$), 5.53 (d, 2H, $^2$J$_{HH}$=15 Hz, CH$_2$), 2.55-0.88 (m, 18H, CH$_3$C$_6$H$_9$CH(CH$_3$)$_2$ & CH$_3$C$_6$H$_9$CH(CH$_3$)$_2$), 1.17 (d, 6H, $^3$J$_{HH}$=7 Hz, CH$_3$C$_6$H$_9$CH(CH$_3$)$_2$), 0.84 (d, 6H, $^3$J$_{HH}$=7 Hz, CH$_3$C$_6$H$_9$CH(CH$_3$)$_2$), 0.74 (d, 6H, $^3$J$_{HH}$=7 Hz, CH$_3$C$_6$H$_9$CH(CH$_3$)$_2$). (Minor) δ 7.60 (s, 2H, N—C(3)H—N), 7.52 (br, 2H, (C$_6$H$_5$), 7.43 (br, 4H, C$_6$H$_5$), 7.33 (br, 4H, C$_6$H$_5$), 5.95 (d, 2H, $^2$J$_{HH}$=15 Hz, CH$_2$), 5.69 (d, 2H, $^2$J$_{HH}$=15 Hz, CH$_2$), 5.65 (br, 2H, CH$_3$C$_6$H$_9$CH(CH$_3$)$_2$), 2.55-0.88 (m, 18H, CH$_3$C$_6$H$_9$CH(CH$_3$)$_2$ & CH$_3$C$_6$H$_9$CH(CH$_3$)$_2$), 1.02 (d, 6H, $^3$J$_{HH}$=7 Hz, CH$_3$C$_6$H$_9$CH(CH$_3$)$_2$), 0.81 (d, 6H, $^3$J$_{HH}$=7 Hz, CH$_3$C$_6$H$_9$CH(CH$_3$)$_2$), 0.64 (d, 6H, $^3$J$_{HH}$=7 Hz, CH$_3$C$_6$H$_9$CH(CH$_3$)$_2$). $^{13}$C{$^1$H}NMR (CDCl$_3$, 100 MHz, 25° C.): (Major) δ 172.5 (Pd—NCN), 141.0 (N—C(3)H—N), 134.8 (ipso-C$_6$H$_5$), 129.3 (C$_6$H$_5$), 129.2 (C$_6$H$_5$), 129.0 (C$_6$H$_5$), 60.8 (CH$_2$), 52.8 (CH$_3$C$_6$H$_9$CH(CH$_3$)$_2$), 47.6 (CH$_3$C$_6$H$_9$CH(CH$_3$)$_2$), 41.5 (CH$_3$C$_6$H$_9$CH(CH$_3$)$_2$), 35.5 (CH$_3$C$_6$H$_9$CH(CH$_3$)$_2$), 29.2 (CH$_3$C$_6$H$_9$CH(CH$_3$)$_2$), 26.2 (CH$_3$C$_6$H$_9$CH(CH$_3$)$_2$), 24.2 (CH$_3$C$_6$H$_9$CH(CH$_3$)$_2$), 23.9 (CH$_3$C$_6$H$_9$CH(CH$_3$)$_2$), 22.6 (CH$_3$C$_6$H$_9$CH(CH$_3$)$_2$), 20.3 (CH$_3$C$_6$H$_9$CH(CH$_3$)$_2$). (Minor) δ 172.5 (Pd—NCN), 140.9 (N—C(3)H—N), 134.6 (ipso-C$_6$H$_5$), 129.0 (C$_6$H$_5$), 128.9 (C$_6$H$_5$), 128.8 (C$_6$H$_5$), 60.6 (CH$_2$), 52.8 (CH$_3$C$_6$H$_9$CH(CH$_3$)$_2$), 47.4 (CH$_3$C$_6$H$_9$CH(CH$_3$)$_2$), 41.4 (CH$_3$C$_6$H$_9$CH(CH$_3$)$_2$), 35.4 (CH$_3$C$_6$H$_9$CH(CH$_3$)$_2$), 29.1 (CH$_3$C$_6$H$_9$CH(CH$_3$)$_2$), 26.2 (CH$_3$C$_6$H$_9$CH(CH$_3$)$_2$), 24.2 (CH$_3$C$_6$H$_9$CH(CH$_3$)$_2$), 23.3 (CH$_3$C$_6$H$_9$CH(CH$_3$)$_2$), 22.6 (CH$_3$C$_6$H$_9$CH(CH$_3$)$_2$), 20.1 (CH$_3$C$_6$H$_9$CH(CH$_3$)$_2$). IR data (KBr pellet) cm$^{-1}$: 3436 (m), 3150 (w), 3054 (w), 2950 (s), 2867 (s), 2844 (m), 1666 (w), 1538 (m), 1498 (w), 1453 (m), 1386 (w), 1367 (m), 1242 (w), 1216 (w), 1201 (w), 980 (w), 938 (w), 775 (w), 718 (m), 660 (w), 474 (w). HRMS (ES): m/z 781.2610 [M−Br]$^+$, calcd. 781.2623. Anal. Calcd. for C$_{38}$H$_{54}$PdBr$_2$N$_6$: C, 53.00; H, 6.32; N, 9.76. Found: C, 53.14; H, 6.87; N, 8.92%. [α]$_D^{25}$ −45.2 (c 1.00 in CHCl$_3$).

Step (e): Synthesis of trans-[1-(1S)-menthyl-4-(benzyl)-1,2,4-triazol-5-ylidene]$_2$Pd(OCOCF$_3$)$_2$ (1S,2S,5R-3c)

A mixture of trans-[1-(1S)-menthyl-4-(benzyl)-1,2,4-triazol-5-ylidene]$_2$PdBr$_2$ (1S,2S,5R-3b) (0.340 g, 0.395 mmol) and AgOCOCF$_3$ (0.192 g, 0.869 mmol) was stirred in CH$_2$Cl$_2$ (ca. 20 mL) at room temperature for 4 hours. The reaction mixture was filtered over celite and solvent was removed under vacuum to obtain the crude product. The crude product was finally purified by column chromatography using silica gel as a stationary phase and eluting with a mixed medium of petroleum ether/EtOAc (90:10 v/v) to give the product 1S,2S,5R-3c as a colourless solid (0.241 g, 66%).

Example 6: Compound—trans-[1-(1S)-menthyl-4-(benzyl)-1,2,4-triazol-5-ylidene]$_2$Pd(OCOCF$_3$)$_2$ (1S, 2S,5R-3c)

Example 6 illustrates the compound trans-[1-(1S)-menthyl-4-(benzyl)-1,2,4-triazol-5-ylidene]$_2$Pd(OCOCF$_3$)$_2$ (1S, 2S,5R-3c), prepared by the process as described in example 5 above and having a formula (Ii) as below:

Formula (Ii)

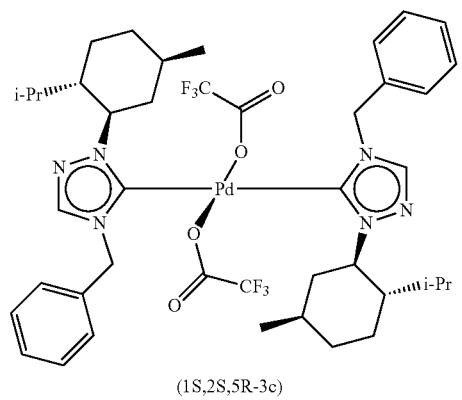

(1S,2S,5R-3c)

Yield: 66%

Spectral data:

$^1$H NMR (CDCl$_3$, 500 MHz, 25° C.): δ 7.63 (br, 2H, N—C(3)H—N), 7.52 (br, 6H, C$_6$H$_5$), 7.30 (br, 4H, C$_6$H$_5$), 6.22 (br, 1H, CH$_2$), 5.99-5.87 (m, 4H, CH$_2$ & CH$_3$C$_6$H$_9$CH(CH$_3$)$_2$), 5.64 (br, 1H, CH$_2$), 2.05-0.62 (m, 18H, CH$_3$C$_6$H$_9$CH(CH$_3$)$_2$ & CH$_3$C$_6$H$_9$CH(CH$_3$)$_2$), 1.12 (br, 6H, CH$_3$C$_6$H$_9$CH(CH$_3$)$_2$), 0.79 (br, 12H, CH$_3$C$_6$H$_9$CH(CH$_3$)$_2$ & CH$_3$C$_6$H$_9$CH(CH$_3$)$_2$). $^{13}$C{$^1$H}NMR (CDCl$_3$, 125 MHz, 25° C.): δ 168.8 (Pd—NCN), 162.3 (q, $^3$J$_{CF}$=40 Hz, OCOCF$_3$), 141.1 (N—C(3)H—N), 134.3 (ipso-C$_6$H$_5$), 129.5 (C$_6$H$_5$), 129.1 (C$_6$H$_5$), 129.1 (C$_6$H$_5$), 114.3 (q, $^2$J$_{CF}$=288 Hz, OCOCF$_3$), 60.8 (CH$_3$C$_6$H$_9$CH(CH$_3$)$_2$), 53.0 (CH$_2$), 47.3 (CH$_3$C$_6$H$_9$CH(CH$_3$)$_2$), 41.5 (CH$_3$C$_6$H$_9$CH(CH$_3$)$_2$), 35.2 (CH$_3$C$_6$H$_9$CH(CH$_3$)$_2$), 29.5 (CH$_3$C$_6$H$_9$CH(CH$_3$)$_2$), 26.1 (CH$_3$C$_6$H$_9$CH(CH$_3$)$_2$), 24.5 (CH$_3$C$_6$H$_9$CH(CH$_3$)$_2$), 22.3 (CH$_3$C$_6$H$_9$CH(CH$_3$)$_2$), 21.7 (CH$_3$C$_6$H$_9$CH(CH$_3$)$_2$), 20.3 (CH$_3$C$_6$H$_9$CH(CH$_3$)$_2$). $^{19}$F{$^1$H}NMR (CDCl$_3$, 470 MHz, 25° C.) δ −73.69 (Pd—OCOCF$_3$). IR data (KBr pellet) cm$^{-1}$: 3114 (w), 3044 (w), 2953 (s), 2929 (m), 2873 (w), 1687 (s), 1574 (w), 1535 (w), 1498 (w), 1456 (w), 1409 (m), 1372 (w), 1305 (w), 1261 (w), 1203 (s), 1183 (s), 1075 (w), 1011 (w), 981 (w), 951 (w), 871 (w), 849 (w), 804 (w), 788 (w), 729 (m), 712 (w), 676 (w). HRMS (ES): m/z 813.3309 [M-OCOCF$_3$]$^+$, calcd. 813.3304. Anal. Calcd. for C$_{42}$H$_{54}$F$_6$N$_6$O$_4$Pd: C, 54.40; H, 5.87; N, 9.06. Found: C, 54.31; H, 5.51; N, 8.65%. [α]$_D^{25}$ +40.2 (c 1.00 in CHCl$_3$).

Example 7: Process for Synthesis of Compound (1R,2R,5S-1c)

Example 7 illustrates the schematic process for preparing enantiomeric form trans-[1-(1R)-menthyl-4-(ethyl)-1,2,4-triazol-5-ylidene]$_2$Pd(OCOCF$_3$)$_2$ (1R,2R,5S-1c).

Process steps involved: —

Steps (a): Synthesis of 1-(1R)-menthyl-1H-1,2,4-triazole (1R,2R,5S-A)

A 250 mL round bottom flask is charged with the compound of 1,2,4-triazole (5.00 g, 72.4 mmol) and (1S,2R,5S)-2-i-propyl-5-methylcyclohexyl 4-methylbenzenesulfonate (10.0 g, 32.2 mmol) in DMF (ca. 100 mL) to which NaH is added portion wise (3.00 g, 125 mmol) at 0° C. The reaction mixture is allowed to stir at room temperature for 30 minutes and then refluxed for 24 hours. After the completion of reaction, the mixture is cooled to room temperature and EtOAc (ca. 500 mL) is added and washed with water (ca. 12×50 mL). The organic layer is collected and vacuum dried to give crude product which is purified by column chromatography using silica gel as a stationary phase and eluting with a petroleum ether/EtOAc mixture (90:10 v/v) to give product (1R,2R,5S-A) as a colourless solid (2.67 g, 40%).

Step (b): Synthesis of 1-(1R)-menthyl-4-(ethyl)-1,2,4-triazolium Bromide (1R,2R,5S-1a)

A mixture of 1-(1R)-menthyl-1H-1,2,4-triazole (1.42 g, 6.85 mmol) (1R,2R,5S-A), and ethyl bromide (3.18 g, 29.2 mmol) is refluxed in acetonitrile (ca. 40 mL) for 24 hours, after which the solvent is removed under vacuum. The residue is washed with hot Et$_2$O (ca. 3×10 mL) and vacuum dried to give the product (1R,2R,5S-1a) as a white solid (0.491 g, 23%).

Step (c, d): Synthesis of trans-[1-(1R)-menthyl-4-(ethyl)-1,2,4-triazol-5-ylidene]$_2$PdBr$_2$ (1R,2R,5S-1b)

A mixture of 1-(1R)-menthyl-4-(ethyl)-1,2,4-triazolium bromide (0.474 g, 1.50 mmol) (1R,2R,5S-1a), PdBr$_2$ (0.200 g, 0.751 mmol) and Et$_3$N (0.606 g, 5.99 mmol) in CH$_3$CN (ca. 50 mL) is refluxed for 12 hours. The reaction mixture is filtered and solvent is removed under vacuum to obtain the product as a yellow colour solid. The crude product is finally purified by column chromatography using silica gel as a stationary phase and eluting with a mixed medium of petroleum ether/EtOAc (85:15 v/v) to give the product 1R,2R,5S-1b as a light yellow solid (0.434 g, 78%). The said compound 1R,2R,5S-1b having formula (Ib) below:

Formula (Ib)

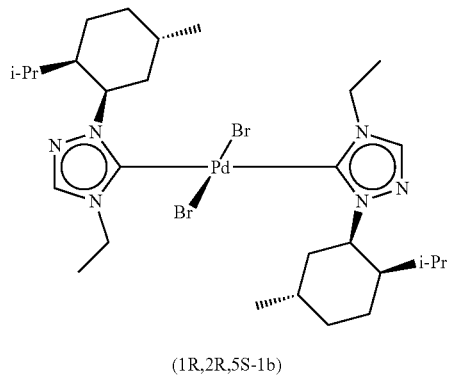

(1R,2R,5S-1b)

Yield: 78%

Spectral data:

$^1$H NMR (CDCl$_3$, 400 MHz, 25° C.): (Major) δ 7.87 (s, 2H, N—C(3)H—N), 5.70 (br, 2H, CH$_3$C$_6$H$_9$CH(CH$_3$)$_2$), 4.78 (qd, 2H, $^3J_{HH}$=7 Hz, CH$_2$CH$_3$), 4.46 (qd, 1H, $^3J_{HH}$=7 Hz, CH$_2$CH$_3$), 2.59-1.00 (m, 18H, CH$_3$C$_6$H$_9$CH(CH$_3$)$_2$ & CH$_3$C$_6$H$_9$CH(CH$_3$)$_2$), 1.73 (t, 6H, $^3J_{HH}$=7 Hz, CH$_2$CH$_3$), 1.12 (d, 6H, $^3J_{HH}$=7 Hz, CH$_3$C$_6$H$_9$CH(CH$_3$)$_2$), 0.85 (d, 6H, $^3J_{HH}$=7 Hz, CH$_3$C$_6$H$_9$CH(CH$_3$)$_2$), 0.74 (d, 6H, $^3J_{HH}$=7 Hz, CH$_3$C$_6$H$_9$CH(CH$_3$)$_2$). (Minor) δ 7.87 (s, 2H, N—C(3)H—N), 5.61 (br, 2H, CH$_3$C$_6$H$_9$CH(CH$_3$)$_2$), 4.74 (qd, 2H, $^3J_{HH}$=7 Hz, CH$_2$CH$_3$), 4.42 (qd, 2H, $^3J_{HH}$=7 Hz, CH$_2$CH$_3$), 2.59-1.00 (m, 18H, CH$_3$C$_6$H$_9$CH(CH$_3$)$_2$ & CH$_3$C$_6$H$_9$CH(CH$_3$)$_2$), 1.71 (t, 6H, $^3J_{HH}$=7 Hz, CH$_2$CH$_3$), 1.09 (d, 6H, $^3J_{HH}$=7 Hz, CH$_3$C$_6$H$_9$CH(CH$_3$)$_2$), 0.84 (d, 6H, $^3J_{HH}$=7 Hz, CH$_3$C$_6$H$_9$CH(CH$_3$)$_2$), 0.72 (d, 6H, $^3J_{HH}$=7 Hz, CH$_3$C$_6$H$_9$CH(CH$_3$)$_2$). $^{13}$C{$^1$H}NMR (CDCl$_3$, 125 MHz, 25° C.): (Major) δ 172.2 (Pd—NCN), 140.7 (N—C(3)H—N), 60.73 (CH$_3$C$_6$H$_9$CH(CH$_3$)$_2$), 47.7 (CH$_3$C$_6$H$_9$CH(CH$_3$)$_2$), 44.1 (CH$_2$CH$_3$), 41.6 (CH$_3$C$_6$H$_9$CH(CH$_3$)$_2$), 35.5 (CH$_3$C$_6$H$_9$CH(CH$_3$)$_2$), 29.1 (CH$_3$C$_6$H$_9$CH(CH$_3$)$_2$), 26.2 (CH$_3$C$_6$H$_9$CH(CH$_3$)$_2$), 24.3 (CH$_3$C$_6$H$_9$CH(CH$_3$)$_2$), 23.35 (CH$_3$C$_6$H$_9$CH(CH$_3$)$_2$), 22.6 (CH$_3$C$_6$H$_9$CH(CH$_3$)$_2$), 20.3 (CH$_3$C$_6$H$_9$CH(CH$_3$)$_2$), 16.1 (CH$_2$CH$_3$). (Minor) δ 172.17 (Pd—NCN), 140.5 (N—C(3)H—N), 60.7 (CH$_3$C$_6$H$_9$CH(CH$_3$)$_2$), 47.6 (CH$_3$C$_6$H$_9$CH(CH$_3$)$_2$), 44.1 (CH$_2$CH$_3$), 41.3 (CH$_3$C$_6$H$_9$CH(CH$_3$)$_2$), 35.5 (CH$_3$C$_6$H$_9$CH(CH$_3$)$_2$), 29.0 (CH$_3$C$_6$H$_9$CH(CH$_3$)$_2$), 26.2 (CH$_3$C$_6$H$_9$CH(CH$_3$)$_2$), 24.2 (CH$_3$C$_6$H$_9$CH(CH$_3$)$_2$), 23.3 (CH$_3$C$_6$H$_9$CH(CH$_3$)$_2$), 22.58 (CH$_3$C$_6$H$_9$CH(CH$_3$)$_2$), 20.3 (CH$_3$C$_6$H$_9$CH(CH$_3$)$_2$), 16.0 (CH$_2$CH$_3$). IR data (KBr pellet) cm$^{-1}$: 3433 (w), 3126 (w), 2950 (s), 2925 (s), 2870 (m), 2848 (m), 1539 (w), 1456 (m), 1373 (w), 1262 (w), 1213 (w), 1097 (w), 1007 (w), 982 (w), 845 (w), 710 (w). HRMS (ES): m/z 657.2302 [M−Br]$^+$, calcd. 657.2308. Anal. Calcd. for C$_{28}$H$_{50}$PdBr$_2$N$_6$: C, 45.63; H, 6.84; N, 11.40. Found: C, 46.06; H, 6.45; N, 11.62%. [α]$_D^{25}$+29.9 (c 1.00 in CHCl$_3$).

Step (e): Synthesis of trans-[1-(1R)-menthyl-4-(ethyl)-1,2,4-triazol-5-ylidene]$_2$Pd(OCOCF$_3$)$_2$ (1R, 2R,5S-1c)

A mixture of trans-[1-(1R)-menthyl-4-(ethyl)-1,2,4-triazol-5-ylidene]$_2$PdBr$_2$ (1R,2R,5S-1b) (0.200 g, 0.271 mmol) and AgOCOCF$_3$ (0.132 g, 0.597 mmol) was stirred in CH$_2$Cl$_2$ (ca. 20 mL) at room temperature for 4 hours. The reaction mixture was filtered over celite and solvent was removed under vacuum to obtain the crude product. The crude product was finally purified by column chromatography using silica gel as a stationary phase and eluting with a mixed medium of petroleum ether/EtOAc (80:20 v/v) to give the product 1R,2R,5S-1c as a colorless solid (0.124 g, 57%).

Example 8: Compound—trans-[1-(1R)-menthyl-4-(ethyl)-1,2,4-triazol-5-ylidene]$_2$Pd(OCOCF$_3$)$_2$ (1R, 2R,5S-1c)

Example 8 illustrates the compound trans-[1-(1R)-menthyl-4-(ethyl)-1,2,4-triazol-5-ylidene]$_2$Pd(OCOCF$_3$)$_2$ (1R, 2R,5S-1c), prepared by the process as described in example 7 above, and having a formula (Ih) below:

Formula (Ih)

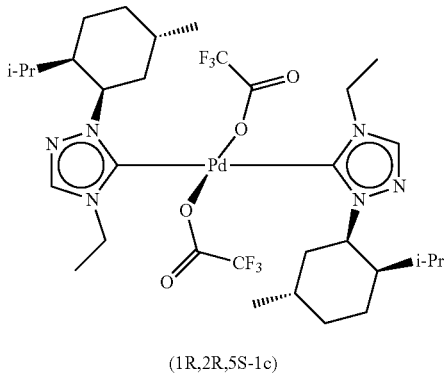

(1R,2R,5S-1c)

Yield: 57%
Spectral data:
$^1$H NMR (CDCl$_3$, 500 MHz, 25° C.): δ 7.93 (s, 2H, N—C(3)H—N), 5.90 (br, 2H, CH$_3$C$_6$H$_9$CH(CH$_3$)$_2$), 4.78 (br, 4H, CH$_2$CH$_3$), 2.09-0.98 (m, 18H, CH$_3$C$_6$H$_9$CH(CH$_3$)$_2$ & CH$_3$C$_6$H$_9$CH(CH$_3$)$_2$), 1.62 (br, 6H, CH$_2$CH$_3$), 1.06 (br, 6H, CH$_3$C$_6$H$_9$CH(CH$_3$)$_2$), 0.74 (d, 6H, $^3J_{HH}$=6 Hz, CH$_3$C$_6$H$_9$CH(CH$_3$)$_2$), 0.74 (br, 6H, CH$_3$C$_6$H$_9$CH(CH$_3$)$_2$). $^{13}$C{$^1$H}NMR (CDCl$_3$, 125 MHz, 25° C.), δ 168.5 (Pd—NCN), 162.3 (q, $^3J_{CF}$=40 Hz, OCOCF$_3$), 140.8 (N—C(3)H—N), 114.1 (q, $^2J_{CF}$=288 Hz, OCOCF$_3$), 60.9 (CH$_3$C$_6$H$_9$CH(CH$_3$)$_2$), 47.5 (CH$_2$CH$_3$), 44.3 (CH$_3$C$_6$H$_9$CH(CH$_3$)$_2$), 41.8 (CH$_3$C$_6$H$_9$CH(CH$_3$)$_2$), 35.6 (CH$_3$C$_6$H$_9$CH(CH$_3$)$_2$), 29.8 (CH$_3$C$_6$H$_9$CH(CH$_3$)$_2$), 26.4 (CH$_3$C$_6$H$_9$CH(CH$_3$)$_2$), 24.8 (CH$_3$C$_6$H$_9$CH(CH$_3$)$_2$), 22.6 (CH$_3$C$_6$H$_9$CH(CH$_3$)$_2$), 22.0 (CH$_3$C$_6$H$_9$CH(CH$_3$)$_2$), 20.4 (CH$_3$C$_6$H$_9$CH(CH$_3$)$_2$), 15.9 (CH$_2$CH$_3$). $^{19}$F{$^1$H}NMR (CDCl$_3$, 470 MHz, 25° C.) δ −73.88 (Pd—OCOCF$_3$). IR data (KBr pellet) cm$^{-1}$: 3445 (m), 3125 (w), 2955 (m), 2926 (m), 2871 (m), 2851 (m), 1695 (s), 1542 (w), 1457 (w), 1406 (w), 1263 (w), 1190 (s), 1149 (s), 1010 (w), 850 (w), 783 (w), 732 (w). HRMS (ES): m/z 689.2988 [M-OCOCF$_3$]$^+$, calcd. 689.2988. Anal. Calcd. for C$_{32}$H$_{50}$F$_6$N$_6$O$_4$Pd: C, 47.85; H, 6.27; N, 10.46. Found: C, 48.26; H, 5.71; N, 10.64%. [α]$_D^{25}$ −48.0 (c 1.00 in CHCl$_3$).

Example 9: Process for Synthesis of Compound (1R,2R,5S-2b)

Example 9 illustrates the schematic process for preparing enantiomeric form trans-[1-(1R)-menthyl-4-(allyl)-1,2,4-triazol-5-ylidene]$_2$PdBr$_2$ (1R,2R,5S-2b).
Process steps involved: —

Steps (a) is Same as Steps (a) of the Process Described in Above Example 7

Step (b): Synthesis of 1-(1R)-menthyl-4-(allyl)-1,2, 4-triazolium Bromide (1R,2R,5S-2a)

A mixture of 1-(1R)-menthyl-1H-1,2,4-triazole (1R,2R, 5S-A) (0.656 g, 3.16 mmol) and allyl bromide (0.384 g, 3.17 mmol) is refluxed in CH$_3$CN (ca. 40 mL) for 24 hours, after which the solvent is removed under vacuum. The residue is washed with hot Et$_2$O (ca. 3×10 mL) and vacuum dried to give the product 1R,2R,5S-2a as a white solid (0.865 g, 83%).

Step (c, d): Synthesis of trans-[1-(1R)-menthyl-4-(allyl)-1,2,4-triazol-5-ylidene]$_2$PdBr$_2$ (1R,2R,5S-2b)

A mixture of 1-(1R)-menthyl-4-(allyl)-1,2,4-triazolium bromide (0.495 g, 1.51 mmol) (1R,2R,5S-2a), PdBr$_2$ (0.200 g, 0.751 mmol) and Et$_3$N (0.606 g, 5.99 mmol) in CH$_3$CN (ca. 50 mL) is refluxed for 12 hours. The reaction mixture is filtered and solvent is removed under vacuum to obtain the product as a yellow colour solid. The crude product is finally purified by column chromatography using silica gel as a stationary phase and eluting with a mixed medium of petroleum ether/EtOAc (88:12 v/v) to give the product/R, 2R,5S-2b as a light yellow solid (0.427 g, 75%).

Example 10: Compound—trans-[1-(1R)-menthyl-4-(allyl)-1,2,4-triazol-5-ylidene]$_2$PdBr$_2$ (1R,2R,5S-2b)

Example 10 illustrates the compound trans-[1-(1R)-menthyl-4-(allyl)-1,2,4-triazol-5-ylidene]$_2$PdBr$_2$ (1R,2R,5S-2b), prepared by the process as described in example 9 above, and having a formula (Id) below:

Formula (Id)

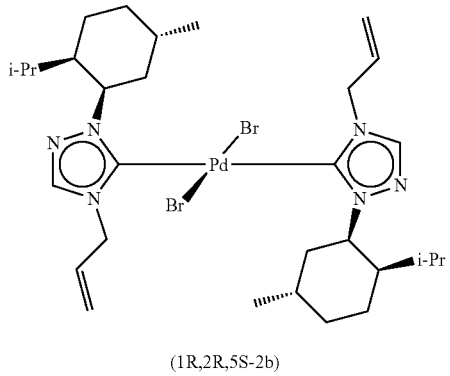

(1R,2R,5S-2b)

Yield: 75%
Spectral data:
$^1$H NMR (CDCl$_3$, 400 MHz, 25° C.): (Major) δ 7.86 (s, 2H, N—C(3)H—N), 6.24 (m, 2H, CH$_2$CH=CH$_2$), 5.73 (br, 2H, CH$_3$C$_6$H$_9$CH(CH$_3$)$_2$), 5.45 (m, 4H, CH$_2$CH=CH$_2$), 5.30 (m, 2H, CH$_2$CH=CH$_2$), 5.07 (qd, 2H, $^2J_{HH}$=15 Hz, $^3J_{HH}$=6 Hz, CH$_2$CH=CH$_2$), 2.59-0.88 (m, 18H, CH$_3$C$_6$H$_9$CH(CH$_3$)$_2$ & CH$_3$C$_6$H$_9$CH(CH$_3$)$_2$), 1.14 (d, 6H, $^3J_{HH}$=7 Hz, CH$_3$C$_6$H$_9$CH(CH$_3$)$_2$), 0.83 (d, 6H, $^3J_{HH}$=7 Hz, CH$_3$C$_6$H$_9$CH(CH$_3$)$_2$), 0.74 (d, 6H, $^3J_{HH}$=7 Hz, CH$_3$C$_6$H$_9$CH(CH$_3$)$_2$). (Minor) 7.86 (s, 2H, N—C(3)H—N), 6.24 (m, 2H, CH$_2$CH=CH$_2$), 5.72 (br, 2H, CH$_3$C$_6$H$_9$CH(CH$_3$)$_2$), 5.40 (m, 4H, CH$_2$CH=CH$_2$), 5.30 (m, 2H, CH$_2$CH=CH$_2$), 5.04 (qd, 2H, $^2J_{HH}$=15 Hz, $^3J_{HH}$=6 Hz, CH$_2$CH=CH$_2$), 2.59-0.88 (m, 18H, CH$_3$C$_6$H$_9$CH(CH$_3$)$_2$ & CH$_3$C$_6$H$_9$CH(CH$_3$)$_2$), 1.08 (d, 6H, $^3J_{HH}$=7 Hz, CH$_3$C$_6$H$_9$CH(CH$_3$)$_2$), 0.83 (d, 6H, $^3J_{HH}$=7 Hz, CH$_3$C$_6$H$_9$CH(CH$_3$)$_2$), 0.71 (d, 6H, $^3J_{HH}$=7 Hz, CH$_3$C$_6$H$_9$CH(CH$_3$)$_2$). $^{13}$C{$^1$H}NMR (CDCl$_3$, 100 MHz, 25° C.): (Major) δ 172.36 (Pd—NCN), 140.91 (N—C(3)H—N), 132.23 (CH$_2$CH=CH$_2$), 120.76 (CH$_2$CH=CH$_2$), 60.73 (CH$_3$C$_6$H$_9$CH(CH$_3$)$_2$), 51.75 (CH$_2$CH=CH$_2$), 47.61 (CH$_3$C$_6$H$_9$CH(CH$_3$)$_2$), 41.61 (CH$_3$C$_6$H$_9$CH(CH$_3$)$_2$), 35.48 (CH$_3$C$_6$H$_9$CH(CH$_3$)$_2$), 29.12 (CH$_3$C$_6$H$_9$CH(CH$_3$)$_2$), 26.19 (CH$_3$C$_6$H$_9$CH(CH$_3$)$_2$), 24.30 (CH$_3$C$_6$H$_9$CH(CH$_3$)$_2$), 23.37 (CH$_3$C$_6$H$_9$CH(CH$_3$)$_2$), 22.61 (CH$_3$C$_6$H$_9$CH(CH$_3$)$_2$), 20.33

($CH_3C_6H_9CH(\underline{C}H_3)_2$). (Minor) δ 172.36 (Pd—N$\underline{C}$N), 140.82 (N—$\underline{C}$(3)H—N), 132.19 $CH_2\underline{C}H=CH_2$, 120.47 ($CH_2CH=\underline{C}H_2$), 60.73 ($CH_3\underline{C}_6H_9CH(CH_3)_2$), 51.67 ($\underline{C}H_2CH=CH_2$), 47.47 ($CH_3\underline{C}_6H_9CH(CH_3)_2$), 41.37 ($CH_3\underline{C}_6H_9CH(CH_3)_2$), 35.48 ($CH_3\underline{C}_6H_9CH(CH_3)_2$), 29.09 ($CH_3\underline{C}_6H_9CH(CH_3)_2$), 26.19 ($CH_3C_6H_9\underline{C}H(CH_3)_2$), 24.14 ($\underline{C}H_3C_6H_9CH(CH_3)_2$), 23.28 ($\underline{C}H_3C_6H_9CH(CH_3)_2$), 22.61 ($CH_3C_6H_9CH(\underline{C}H_3)_2$), 20.25 ($CH_3C_6H_9CH(\underline{C}H_3)_2$). IR data (KBr pellet) cm$^{-1}$: 3445 (w), 3123 (w), 2953 (s), 2925 (s), 2869 (s), 2846 (m), 1645 (w), 1538 (m), 1453 (m), 1444 (m), 1370 (m), 1202 (w), 1009 (w), 983 (m), 938 (m), 919 (w), 845 (w), 787 (m), 717 (w), 667 (m) 562 (w). HRMS (ES): m/z 681.2301 [M−Br]$^+$, calcd. 681.2308. Anal. Calcd. for $C_{30}H_{50}PdBr_2N_6$: C, 47.35; H, 6.62; N, 11.04. Found: C, 47.75; H, 6.37; N, 11.13%. $[\alpha]_D^{25}$+39.6 (c 1.00 in $CHCl_3$).

Example 11: Process for Synthesis of Compound (1R,2R,5S-3b)

Example 11 illustrates the schematic process for preparing enantiomeric form trans-[1-(1R)-menthyl-4-(benzyl)-1,2,4-triazol-5-ylidene]$_2$PdBr$_2$ (1R,2R,5S-3b).

Process steps involved: —

Steps (a) is Same as Steps (a) of the Process Described in Above Example 7

Step (b): Synthesis of 1-(1R)-menthyl-4-(benzyl)-1,2,4-triazolium Bromide (1R,2R,5S-3a)

A mixture of 1-(1R)-menthyl-1H-1,2,4-triazole (1R,2R,5S-A) (0.800 g, 3.86 mmol) and benzyl bromide (0.660 g, 3.86 mmol) is refluxed in $CH_3CN$ (ca. 40 mL) for overnight, after which the solvent is removed under vacuum. The residue is washed with hot $Et_2O$ (ca. 3×10 mL) and vacuum dried to give the product 1R,2R,5S-3a as a white solid (1.164 g, 80%).

Step (c, d): Synthesis of trans-[1-(1R)-menthyl-4-(benzyl)-1,2,4-triazol-5-ylidene]$_2$PdBr$_2$ (1R,2R,5S-3b)

A mixture of 1-(1R)-menthyl-4-(benzyl)-1,2,4-triazolium bromide (1R,2R,5S-3a) (0.568 g, 1.50 mmol), PdBr$_2$ (0.200 g, 0.751 mmol) and Et$_3$N (0.606 g, 5.99 mmol) in $CH_3CN$ (ca. 50 mL) is refluxed for 12 hours. The reaction mixture is filtered and solvent is removed under vacuum to obtain the product as a yellow colour solid. The crude product is finally purified by column chromatography using silica gel as a stationary phase and eluting with a mixed medium of petroleum ether/EtOAc (88:12 v/v) to give the product 1R,2R,5S-3b as a light yellow solid (0.511 g, 79%).

Example 12: Compound trans-[1-(1R)-menthyl-4-(benzyl)-1,2,4-triazol-5-ylidene]$_2$PdBr$_2$ (1R,2R,5S-3b)

Example 12 illustrates the compound trans-[1-(1R)-menthyl-4-(benzyl)-1,2,4-triazol-5-ylidene]$_2$PdBr$_2$ (1R,2R,5S-3b), prepared by the process as described in example 11 above, and having a formula (If) below:

Formula (If)

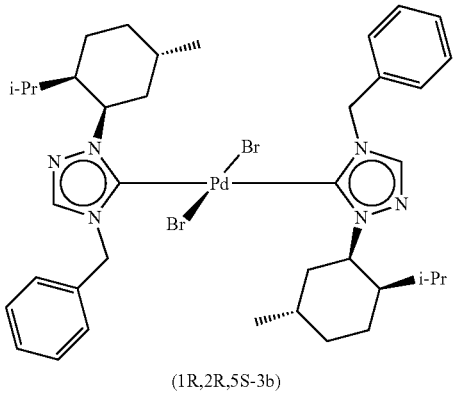

(1R,2R,5S-3b)

Yield: 79%

Spectral data:

1H NMR (CDCl$_3$, 400 MHz, 25° C.): (Major) δ 7.65 (s, 2H, N—C(3)$\underline{H}$—N), 7.53 (br, 2H, (C$_6\underline{H}_5$), 7.45 (br, 4H, C$_6\underline{H}_5$), 7.35 (br, 4H, C$_6\underline{H}_5$), 5.93 (br, 2H, C$\underline{H}_2$), 5.67 (br, 2H, $CH_3C_6\underline{H}_9CH(CH_3)_2$), 5.53 (br, 2H, C$\underline{H}_2$), 2.55-0.88 (m, 18H, $CH_3C_6\underline{H}_9CH(CH_3)_2$ & $CH_3C_6H_9C\underline{H}(CH_3)_2$), 1.17 (d, 6H, $^3J_{HH}$=7 Hz, $CH_3C_6H_9CH(C\underline{H}_3)_2$), 0.84 (d, 6H, $^3J_{HH}$=7 Hz, $CH_3C_6H_9CH(C\underline{H}_3)_2$), 0.74 (d, 6H, $^3J_{HH}$=7 Hz, C$\underline{H}_3C_6H_9CH(CH_3)_2$). (Minor) δ 7.60 (s, 2H, N—C(3)$\underline{H}$—N), 7.52 (br, 2H, (C$_6\underline{H}_5$), 7.43 (br, 4H, C$_6\underline{H}_5$), 7.33 (br, 4H, C$_6\underline{H}_5$), 5.95 (br, 2H, C$\underline{H}_2$), 5.69 (br, 2H, C$\underline{H}_2$), 5.65 (br, 2H, $CH_3C_6\underline{H}_9CH(CH_3)_2$), 2.55-0.88 (m, 18H, $CH_3C_6\underline{H}_9CH(CH_3)_2$ & $CH_3C_6H_9C\underline{H}(CH_3)_2$), 1.02 (d, 6H, $^3J_{HH}$=7 Hz, $CH_3C_6H_9CH(C\underline{H}_3)_2$), 0.81 (d, 6H, $^3J_{HH}$=7 Hz, $CH_3C_6H_9CH(C\underline{H}_3)_2$), 0.64 (d, 6H, $^3J_{HH}$=7 Hz, C$\underline{H}_3C_6H_9CH(CH_3)_2$). $^{13}C\{^1H\}$NMR (CDCl$_3$, 100 MHz, 25° C.): (Major) δ 172.5 (Pd—N$\underline{C}$N), 141.0 (N—$\underline{C}$(3)H—N), 134.8 (ipso-$\underline{C}_6H_5$), 129.3 ($\underline{C}_6H_5$), 129.23 ($\underline{C}_6H_5$), 129.20 ($\underline{C}_6H_5$), 60.8 ($\underline{C}H_2$), 52.8 ($CH_3\underline{C}_6H_9CH(CH_3)_2$), 47.6 ($CH_3\underline{C}_6H_9CH(CH_3)_2$), 41.5 ($CH_3\underline{C}_6H_9CH(CH_3)_2$), 35.4 ($CH_3\underline{C}_6H_9CH(CH_3)_2$), 29.2 ($CH_3\underline{C}_6H_9CH(CH_3)_2$), 26.2 ($CH_3C_6H_9\underline{C}H(CH_3)_2$), 24.2 ($\underline{C}H_3C_6H_9CH(CH_3)_2$), 23.9 ($\underline{C}H_3C_6H_9CH(CH_3)_2$), 22.6 ($CH_3C_6H_9CH(\underline{C}H_3)_2$), 20.3 ($CH_3C_6H_9CH(\underline{C}H_3)_2$). (Minor) δ 172.46 (Pd—N$\underline{C}$N), 140.9 (N—$\underline{C}$(3)H—N), 134.6 (ipso-$\underline{C}_6H_5$), 129.0 ($\underline{C}_6H_5$), 128.9 ($\underline{C}_6H_5$), 128.8 ($\underline{C}_6H_5$), 60.8 ($\underline{C}H_2$), 52.76 ($CH_3\underline{C}_6H_9CH(CH_3)_2$), 47.4 ($CH_3\underline{C}_6H_9CH(CH_3)_2$), 41.4 ($CH_3\underline{C}_6H_9CH(CH_3)_2$), 35.44 ($CH_3\underline{C}_6H_9CH(CH_3)_2$), 29.1 ($CH_3\underline{C}_6H_9CH(CH_3)_2$), 26.18 ($CH_3C_6H_9\underline{C}H(CH_3)_2$), 23.99 ($\underline{C}H_3C_6H_9CH(CH_3)_2$), 23.33 ($\underline{C}H_3C_6H_9CH(CH_3)_2$), 22.6 ($CH_3C_6H_9CH(\underline{C}H_3)_2$), 20.1 ($CH_3C_6H_9CH(\underline{C}H_3)_2$). IR data (KBr pellet) cm$^{-1}$: 3444 (m), 2951 (s), 2919 (s), 2867 (m), 2847 (w), 1634 (w), 1538 (w), 1498 (w), 1455 (m), 1431 (m), 1387 (w), 1369 (m), 1216 (w), 1200 (w), 1008 (w), 985 (w), 938 (w), 719 (s), 660 (w). HRMS (ES): m/z 781.2593 [M−Br]$^+$, calcd. 781.2623. Anal. Calcd. for $C_{38}H_{54}PdBr_2N_6$: C, 53.00; H, 6.32; N, 9.76. Found: C, 53.65; H, 6.21; N, 9.57%. $[\alpha]_D^{25}$+45.0 (c 1.00 in $CHCl_3$).

Example 13: Process for Synthesis of Compound (1R,2R,5S-3c)

Example 13 illustrates the process for preparing enantiomeric form trans-[1-(1R)-menthyl-4-(benzyl)-1,2,4-triazol-5-ylidene]$_2$Pd(OCOCF$_3$)$_2$ (1R,2R,5S-3c).

Process steps involved: —

Steps (a, b c) are Same as Steps (a, b, c) of the Process Described in Example 11 Above Step (e): Synthesis of trans-[1-(1R)-menthyl-4-(benzyl)-1,2,4-triazol-5-ylidene]$_2$Pd(OCOCF$_3$)$_2$ (1R,2R, 5S-3c)

A mixture of trans-[1-(1R)-menthyl-4-(benzyl)-1,2,4-triazol-5-ylidene]$_2$PdBr$_2$ (1R,2R,5S-3b) (0.250 g, 0.290 mmol) and AgOCOCF$_3$ (0.141 g, 0.639 mmol) was stirred in CH$_2$Cl$_2$ (ca. 20 mL) at room temperature for 4 hours. The reaction mixture was filtered over celite and solvent was removed under vacuum to obtain the crude product. The crude product was finally purified by column chromatography using silica gel as a stationary phase and eluting with a mixed medium of petroleum ether/EtOAc (90:10 v/v) to give the product/R,2R,5S-3c as a colorless solid (0.157 g, 58%).

Example 14: Compound—trans-[1-(1R)-menthyl-4-(benzyl)-1,2,4-triazol-5-ylidene]$_2$Pd(OCOCF$_3$)$_2$ (1R, 2R,5S-3c)

Example 14 illustrates the compound trans-[1-(1R)-menthyl-4-(benzyl)-1,2,4-triazol-5-ylidene]$_2$Pd(OCOCF$_3$)$_2$ (1R, 2R,5S-3c), prepared by the process as described in example 13 above, and having a formula (Ij) below:

Formula (Ij)

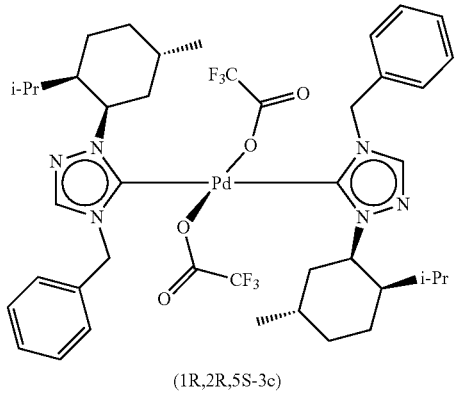

(1R,2R,5S-3c)

Yield: 58%
Spectral data:
$^1$H NMR (CDCl$_3$, 400 MHz, 25° C.): δ 7.63 (br, 2H, N—C(3)H—N), 7.32 (br, 6H, C$_6$H$_5$), 7.30-7.28 (m, 4H, C$_6$H$_5$), 6.22 (br, 2H, CH$_2$), 5.99-5.87 (m, 4H, CH$_2$ & CH$_3$C$_6$H$_9$CH(CH$_3$)$_2$), 5.64 (br, 2H, CH$_2$), 2.05-0.62 (m, 18H, CH$_3$C$_6$H$_9$CH(CH$_3$)$_2$ & CH$_3$C$_6$H$_9$CH(CH$_3$)$_2$), 1.12 (br, 6H, CH$_3$C$_6$H$_9$CH(CH$_3$)$_2$), 0.79 (br, 12H, CH$_3$C$_6$H$_9$CH(CH$_3$)$_2$ & CH$_3$C$_6$H$_9$CH(CH$_3$)$_2$). $^{13}$C{$^1$H}NMR (CDCl$_3$, 100 MHz, 25° C.): δ 168.8 (Pd—NCN), 162.4 (q, $^3J_{CF}$=40 Hz, OCOCF$_3$), 141.1 (N—C(3)H—N), 134.3 (ipso-C$_6$H$_5$), 129.5 (C$_6$H$_5$), 129.13 (C$_6$H$_5$), 129.08 (C$_6$H$_5$), 114.3 (q, $^2J_{CF}$=288 Hz, OCOCF$_3$), 60.8 (CH$_3$C$_6$H$_9$CH(CH$_3$)$_2$), 53.0 (CH$_2$), 47.2 (CH$_3$C$_6$H$_9$CH(CH$_3$)$_2$), 41.5 (CH$_3$C$_6$H$_9$CH(CH$_3$)$_2$), 35.2 (CH$_3$C$_6$H$_9$CH(CH$_3$)$_2$), 29.9 (CH$_3$C$_6$H$_9$CH(CH$_3$)$_2$), 26.1 (CH$_3$C$_6$H$_9$CH(CH$_3$)$_2$), 24.4 (CH$_3$C$_6$H$_9$CH(CH$_3$)$_2$), 22.3 (CH$_3$C$_6$H$_9$CH(CH$_3$)$_2$), 21.7 (CH$_3$C$_6$H$_9$CH(CH$_3$)$_2$), 20.3 (CH$_3$C$_6$H$_9$CH(CH$_3$)$_2$). $^{19}$F{$^1$H}NMR (CDCl$_3$, 470 MHz, 25° C.) δ −73.69 (Pd—OCOCF$_3$). IR data (KBr pellet) cm$^{-1}$: 3444 (m), 3114 (w), 2952 (s), 2925 (m), 2873 (m), 2847 (w), 1687 (s), 1536 (w), 1456 (m), 1409 (m), 1375 (w), 1184 (s), 1010 (w), 849 (w), 788 (w), 729 (m), 714 (m), 694 (w). HRMS (ES): m/z 813.3306 [M-OCOCF$_3$]$^+$, calcd. 813.3304. Anal. Calcd. for C$_{42}$H$_{54}$F$_6$N$_6$O$_4$Pd: C, 54.40; H, 5.87; N, 9.06. Found: C, 53.76; H, 5.59; N, 8.72%. [α]$_D^{25}$−44.4 (c 1.00 in CHCl$_3$).

Example 15: In Vitro Study for Anti-Cancer Activities of the Present Pd—NHC Compounds Against Human Cell Lines Experiment: The anti-proliferative activity of the present palladium N-heterocyclic carbene complexes on two different cancer cell lines MCF-7 and HeLa is tested using Sulforhodamine B assay to reveal their anti-tumor properties. The evaluation of growth inhibition of these complexes is done from their IC$_{50}$ values for the inhibition of cell growth. The IC$_{50}$ values are compared with Cisplatin to determine any increase in efficacy.

Method: The effects of present series of palladium N-heterocyclic carbene complexes, such as compounds (1S,2S, 5R)-(1-3)b and (1R,2R,5S)-(1-3)b; (1S,2S,5R)-(1, 3)c and (1R,2R,5S)-(1, 3)c on the proliferation of MCF-7 cells after one cell cycle are determined by Sulforhodamine B assay. In particular, 1×10$^5$ cells/mL are seeded in each well in 96-well plates for 24 h and then incubated without or with different concentrations of these complexes at 37° C. for one cell cycle (48 h). After incubation of cells with the complexes for one cell cycle, cell growth is stopped by the addition of 50% trichloroacetic acid and stained with 0.4% sulforhodamine B dissolved in 1% acetic acid. Unbound dye is removed by washing with 1% acetic acid, and the protein content is determined by measuring absorbance at 520 nm in a Bio-Rad model 680 microplate reader after extracting with 10 mM tris base. Data are the averages of three independent experiments (as shown in Table 1 below). IC$_{50}$ value is calculated as the concentration of the complex that inhibited the proliferation of cells by 50% relative to the untreated control cells. The anticancer activities of the present Pd—NHC compounds are graphically represented in accompanying FIG. 1.

Results: Anticancer activity of chiral Pd—NHC complexes, (1S,2S,5R)-(1-3)b and (1R,2R,5S)-(1-3)b; (1S,2S, 5R)-(1, 3)c and (1R,2R,5S)-(1, 3)c, against MCF-7 breast cancer cells have been analyzed, graphically plotted (as shown in accompanying FIG. 1) and the results obtained is depicted in table 1 below:

TABLE 1
| S. No. | Compound | $[\alpha]_D^{25}$ | IC$_{50}$ (μM) | Compound | $[\alpha]_D^{25}$ | IC$_{50}$ (μM) |
|---|---|---|---|---|---|---|
| 1 | 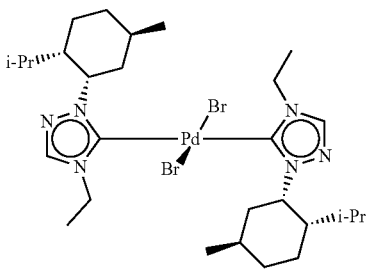<br>(1S,2S,5R)-1b | −29.4 | 2.2 ± 0.1 | 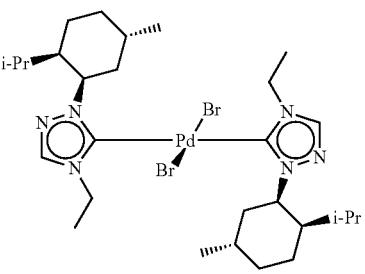<br>(1R,2R,5S)-1b | +29.8 | 2.3 ± 1 |
| 2 | 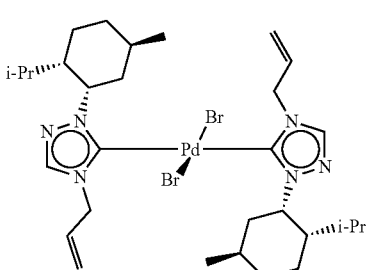<br>(1S,2S,5R)-2b | −41.7 | ≈10 | 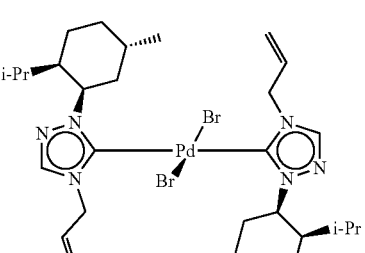<br>(1R,2R,5S)-2b | +39.4 | ≈10 |
| 3 | 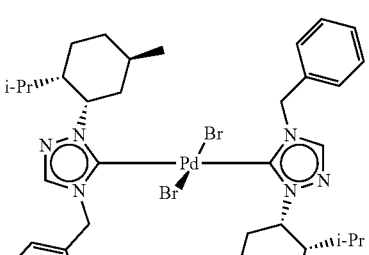<br>(1S,2S,5R)-3b | −45.2 | >10 | 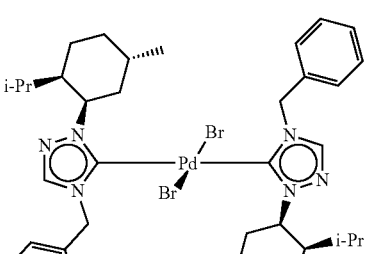<br>(1R,2R,5S)-3b | +45.0 | >10 |
| 4 | 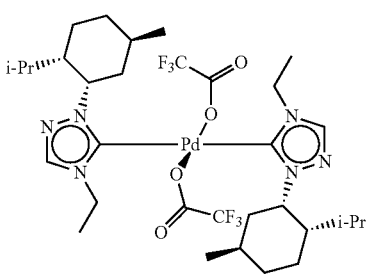<br>(1S,2S,5R)-1c | +47.8 | 700 ± 5 nM | 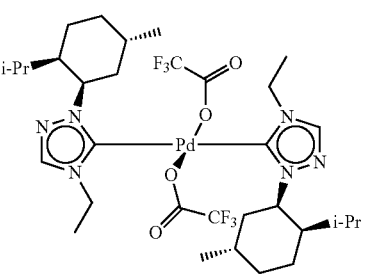<br>(1R,2R,5S)-1c | −48.0 | 550 ± 20 nM |

TABLE 1-continued

| S. No. | Compound | $[\alpha]_D^{25}$ | IC$_{50}$ (µM) | Compound | $[\alpha]_D^{25}$ | IC$_{50}$ (µM) |
|---|---|---|---|---|---|---|
| 5 | (1S,2S,5R)-3c | +40.2 | >10 | (1R,2R,5S)-3c | −44.4 | >10 |

According to that graphical data, the most potent of these compounds, (1R,2R,5S-1c) is found to inhibit the cell proliferation of MCF-7 with an IC$_{50}$ of 550±20 nM.

Similarly, the effect of most potent enantiomeric pair—(1S,2S,5R-1c) and (1R,2R,5S-1c), on HeLa cell lines is determined. The seeded cells in 96-well plates are incubated with the complex for 24 h and the assay is performed. The complexes inhibited cell proliferation of HeLa cells in the range of IC$_{50}$ of 2.3±1 µM to 2.6±1.6 µM.

Example 16: Comparative Anti-Cancer Potency of the Present Compounds with Standard Drug Cisplatin Example 16 provides a comparative data between the anti-cancer efficiencies of the most potent enantiomeric pair—(1S,2S,5R-1c) and (1R,2R,5S-1c) of the present Pd—NHC series and that of Cisplatin, the platinum (Pt) based standard drug in market.

Experiment: In order to compare the potency of the most active enantiomeric pair-(1S,2S,5R-1c) and (1R,2R,5S-1c) of the present Pd—NHC complexes with that of Cisplatin, the MCF-7 and HeLa cells are treated with said Pd—NHC complexes and Cisplatin and the assay is performed simultaneously. The data obtained is graphically represented in accompanying FIG. 2.

Results: The results obtained are graphically compared and the comparative data is provided in table 2 below:

TABLE 2

Anticancer activity of chiral Pd-NHC complexes (1S,2S,5R)-1c and (1R,2R,5S)-1c, and cisplatin against MCF-7 and HeLa cells.

| S. No. | compound | MCF-7 IC$_{50}$ (µM) | Hela IC$_{50}$ (µM) |
|---|---|---|---|
| 1 | (1S,2S,5R)-1c | 700 ± 5 nM | 2.6 ± 1.6 |

TABLE 2-continued

Anticancer activity of chiral Pd-NHC complexes (1S,2S,5R)-1c and (1R,2R,5S)-1c, and cisplatin against MCF-7 and HeLa cells.

| S. No. | compound | MCF-7 IC$_{50}$ (μM) | Hela IC$_{50}$ (μM) |
|---|---|---|---|
| 2 | (1R,2R,5S)-1c | 550 ± 20 nM | 2.3 ± 1 |
| 3 | cisplatin | 14.9 ± 0.4 | 8.5 ± 0.7 |

According to the data in table 2 above, the IC$_{50}$ value of Cisplatin against MCF-7 is found to be 14.9±0.4 μM which is ~27 times as compared to IC$_{50}$ value of the potent complex (1R,2R,5S-1c). Further, the IC$_{50}$ value of Cisplatin against HeLa is found to be 8.5±0.7 μM, which is around 4 times the IC$_{50}$ value of the potent complex (1R,2R,5S-1c). Therefore, the comparative data in table 2 above evidently shows that the enantiomeric pair—(1S,2S,5R-1c) and (1R, 2R,5S-1c) of the present Pd—NHC series is significantly superior in anti-cancer activity in view of the standard drug Cisplatin.

Example 17: In Vitro Study for Anti-Cancer Activities of the Most Potent Isomer (1R,2R,5S-1c) Against Other Human Cell Lines Example 17 demonstrates the expediency of anti-cancer activity of the most potent compound in the series (1R,2R, 5S)-1c which is further tested against additional cell lines namely, lung cancer cells (A549), skin cancer cell (B16-F10) and multi drug resistant cancer cells, EMT6/AR1.

Experiment: The anti-proliferative activity of the most potent compound in the series (1R,2R,5S)-1c is tested against different cancer cell lines A549, B16-F10 and EMT6/AR1 using Sulforhodamine B assay to reveal their anti-tumour properties.

Results: Anticancer activity of the most potent compound in the series (1R,2R,5S)-1c is found to exhibit high cytotoxic activity against A549 cancer cell lines with the IC$_{50}$ value ranging between 4.1 μM and 7.3 μM; and against B16-F10 cancer cell lines with the IC$_{50}$ value ranging between 0.9 μM and 1.7 μM and, graphically plotted in accompanying FIG. 3. The complex inhibited cell proliferation of EMT6/AR1 cells in the range of IC$_{50}$ of 4.5 μM to 5.1 μM. The results obtained is depicted in table 3 below:

TABLE 3

Overall anticancer activity of the most potent complex (1R,2R,5S)-1c against various cancer cell lines.

| | | IC$_{50}$ (μM) values | | | | |
|---|---|---|---|---|---|---|
| S. No | Compound | MCF-7 (breast cancer cells) | HeLa (cervical cancer cells) | A549 (lung cancer cells) | B16-F10 (skin cancer cells) | EMT6/AR1 (multidrug resistant mammary cancer) |
| 1 | (1R,2R,5S)-1c | 550 ± 20 nM | 2.3 ± 1 | 5.7 ± 1.6 | 1.3 ± 0.4 | 4.8 ± 0.3 |

Example 18: In Vitro Study for Selectivity of the Most Potent Isomer (1R,2R,5S-1c) Towards Normal and Cancer Cell Lines Example 18 demonstrates that the current Pd—NHC compounds possess higher selectivity towards the cancer cells over the normal cell lines.

Experiment: In order to check the selectivity between the normal and cancer cells the most potent compound in the series (1R,2R,5S)-1c is tested against skin cancer cell (B16-F10) and the normal skin cell (L929) and breast cancer cells (MCF-7) and the normal epithelial breast cells (MCF10A).

Results: The comparative activity profile for the potent compound (1R,2R,5S)-1c against skin cancer cells (B16-F10) and normal skin cells (L929) and breast cancer cells (MCF-7) and the normal epithelial breast cells (MCF10A) have been tested and graphically plotted as shown in accompanying FIG. 4. The present potent compound of series (1R,2R,5S)-1c is found to exhibit cytotoxic activity against B16-F10 cancer cell lines with the $IC_{50}$ value ranging between 0.9 μM and 1.7 μM and for the L929 normal cell lines with the $IC_{50}$ value ranging between 10.3 μM and 10.7 μM which is around 8.1 times more selective towards the cancer cells. The present potent compound (1R,2R,5S)-1c is found to exhibit cytotoxic activity against MCF-7 cancer cell lines with the $IC_{50}$ value ranging between 0.53 μM and 0.57 μM and for the MCF10A normal cell lines with the $IC_{50}$ value ranging between 7.7 μM and 9.5 μM which is around 16 times more selective towards the cancer cells.

Example 19: Comparative Anti-Cancer Potency of the Present Compounds with that of the Closest Prior Arts Example 19 provides a comparative data between the anti-cancer efficiencies of the most potent enantiomeric pair—(1S,2S,5R-1c) and (1R,2R,5S-1c) of the present Pd—NHC series and the Pd—NHC complexes reported in the prior arts, as described below: (a) Ghosh, P. et. al.: *J. Am. Chem. Soc.* 2007, 129, 15042-15053 discloses superior anticancer activities of the imidazole based Pd—NHC complexes over Cisplatin. The trans-(NHC)nPd(pyridine)mCl₂ complexes disclosed in this prior publication are as under:

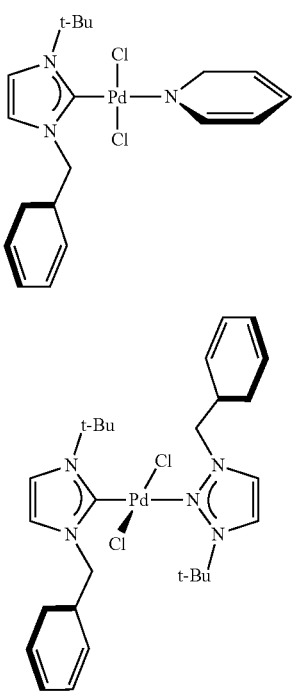

1a

1b

According to scheme 1 of page 15045 of this article, the two trans-(NHC)nPd(pyridine)mCl₂ complexes 1a and 1b were synthesized using different pathways: 1a was synthesized by a direct reaction of 1-benzyl-3-tert-butylimidazolium chloride with PdCl₂ in pyridine, while 1b was obtained from the silver complex 1d by treatment with (COD)-PdCl₂, employing a frequently used carbene-transfer route. Formations of 1a and 1b was confirmed by the appearance of the diagnostic metal-bound carbene (NCN—Pd) resonances at 151.4 ppm (1a) and 166.9 ppm (1b) in their respective $^{13}C\{^1H\}$ NMR spectrum.

Inhibition of cell proliferation was examined by incubating cells with different concentrations of 1b or cisplatin for one cell cycle, and the cell proliferation was measured by the standard sulforhodamine B assay. 1b had a stronger inhibition effect on the proliferation of HeLa, MCF-7, and HCT 116 cells than cisplatin under similar experimental conditions [Table 2, FIG. 2 of prior art (a)]. $IC_{50}$ values of cisplatin for HeLa, MCF-7, and HCT 116 were 8, 15, and 16 μM respectively, whereas the corresponding values for 1b were 4, 1, and 0.8 μM respectively [Table 2, FIG. 2 of prior art (a)].

(b) Haque et. al.: *Metallomics*, 2013, 5, 760-769 reveals chlorine (Cl)—Pd—NHC complex mimicking Pt-based NHC complexes like Cisplatin and its superior anti-cancer activity over Cisplatin. The Pd—NHC complexes disclosed in this prior publication are as under:

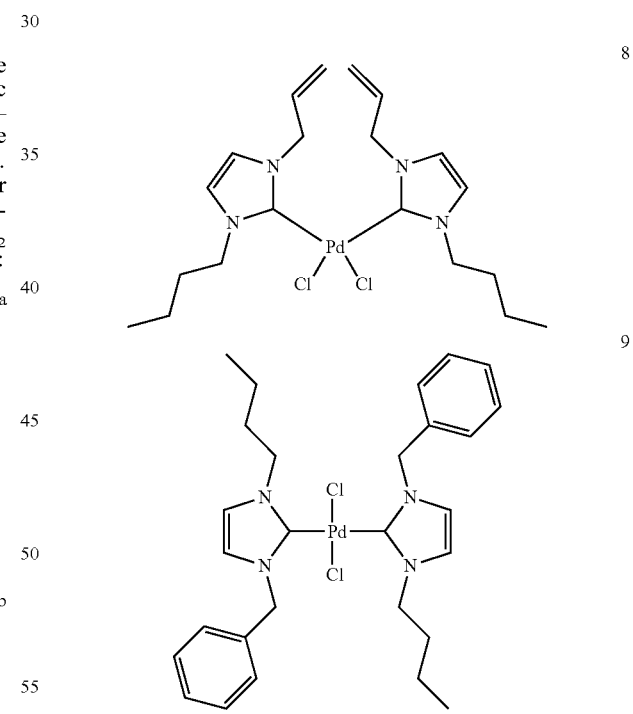

8

9

According to paragraph 2.1.3 and scheme 2 of page 762 of this article, the synthesis of Pd—NHC complexes 7 to 9 was achieved by transmetallation. The corresponding Ag(I)—NHC complexes 4 to 6 were treated with [PdCl₂(CH₃CN)₂] in stirring dichloromethane for 4 hours for complexes 8 and 9.

According to paragraph 2.4, page 765 of the article, in vitro anticancer activities of the prepared Pd—NHC complexes were determined against HCT 116 cell lines based on the MTT assay method using 5-fluorouracil (5-FU) as an internal standard. After an incubation period of 72 hours at different concentrations, only complexes 8 and 9 showed anticancer activities against the tested cell line, with $IC_{50}$ values of 26.5 and 6.6 µM, respectively.

Thus the table 4 below provides the comparative data between the anticancer activities achieved by the present Pd—NHC compounds prepared by the present process and those for the compounds of prior arts (a) and (b):

TABLE 4

| Sl. No. | Prior Arts | Pd-NHC compounds | MCF-7 ($IC_{50}$ value) | HeLa ($IC_{50}$ value) | HCT-116 ($IC_{50}$ value) |
|---|---|---|---|---|---|
| 1 | Ghosh, P. et. al.: *J. Am. Chem. Soc.* 2007, 129, 15042-15053 | FIG. 1(b), page 15044 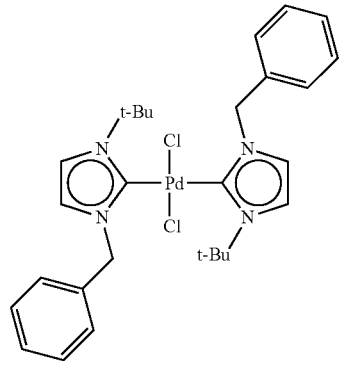 Imidazole derived NHC | 1 ± 3 µM | 4 ± 0.2 µM | 0.8 ± 0.05 µM |
| 2 | Haque et. al.: *Metallomics*, 2013, 5, 760-769 | Pd(II)-NHC Complex 8, page 762 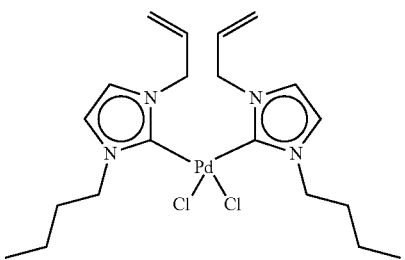 Pd(II)-NHC Complex 9, page 762 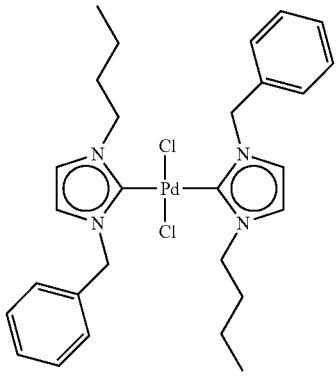 | — | — | 6.6-26.5 µM |

TABLE 4-continued

| Sl. No. | Prior Arts | Pd-NHC compounds | MCF-7 ($IC_{50}$ value) | HeLa ($IC_{50}$ value) | HCT-116 ($IC_{50}$ value) |
|---|---|---|---|---|---|
| 3 | Present invention | Compounds (1S,2S,5R-1c): (1S,2S,5R)-1c | 0.7 ± 0.005 µM | 2.6 ± 1.6 µM | — |
| | | Compound (1R,2R,5S-1c): (1R,2R,5S)-1c | 0.55 ± 0.02 µM | 2.3 ± 1 µM | — |

The comparative data in above table 4 evidently shows that the present Pd—NHC complexes exhibits superior anti-cancer activities against MCF-7 and HeLa cell lines in terms of the imidazole based Pd—NHC complexes reported in the prior arts (a) and (b) [Table 4, entries 1 and 2].

Example 20: Western Blot Analysis for PARP Cleavage and Flow Cytometry for Live Dead Assay Experiment: MCF-7 cells (5 mL) were seeded at a density of $1.5 \times 10^5$ cells/mL in 60 mm cell culture dishes. After cell attachment, they were incubated with 4 and 8 µM (1R,2R,5S)-1c and 4 µM cisplatin for 48 h. The cells were then processed and the whole cell lysate was isolated. An equal amount of total protein was resolved on SDS-PAGE and electroblotted onto a PVDF membrane (Millipore). Immunoblotting was performed using specific antibodies against PARP-1 and β-actin. The blots were developed by chemiluminescence using HRP conjugated secondary IgG.

MCF-7 cells (5 mL) were seeded in 60 mm cell culture dishes at a density of $1.5 \times 10^5$ cells/mL. Cells were incubated with 4 and 8 µM (1R,2R,5S)-1c for 48 h for live dead assay. After the required incubation, cells were processed and analyzed by flow cytometry. Percentage of live and dead MCF-7 cells in the absence and presence of 4 and 8 µM (1R,2R,5S)-1c and 4 µM cisplatin was determined by flow cytometry using propidium iodide (PI).

Results: The result for live-dead cell assay is graphically illustrated in FIG. 5A. PI stained dead cells, while the live cells remained unstained. Data are average of three independent set of experiments and ±indicates S.D. The percentage of live and dead MCF-7 cells after (1R,2R,5S)-1c treatment is also provided in Table 5. Also as seen from FIG. 5B, (1R,2R,5S)-1c cleaves PARP in MCF-7 cells indicating apoptosis of cells.

TABLE 5

Percentage of live and dead MCF-7 cells after (1R,2R,5S)-1c treatment.

| S. No | Samples | Live % | Dead % |
|---|---|---|---|
| 1 | Control | 98 ± 1 | 2 ± 1 |
| 2 | 4 µM (1R,2R,5S)-1c | 59 ± 2 | 41 ± 2 |
| 3 | 8 µM (1R,2R,5S)-1c | 10 ± 1 | 90 ± 1 |
| 4 | 4 µM cisplatin | 93 ± 4 | 8 ± 2 |

Example 21: Immunofluorescence Microscopy for DNA Damage

Experiment: MCF-7 ($5 \times 10^4$ cells/well) cells were seeded on glass cover slip in a 24 well cell culture plate. After the cell were attached, they were incubated with 4 and 8 µM (1R,2R,5S)-1c and 4 µM cisplatin for 36 h, fixed with 3.7% formaldehyde and processed for immunostaining. After fixing, cells were blocked with 2% BSA and incubated with anti-γ $H_2AX$ IgG (1:200) for 2 h at 37° C. followed by Alexa flour 555 goat anti-rabbit secondary IgG (1:400) for 1 h at 37° C. Hoechst 33258 was used to stain the DNA. Immunofluorescence imaging was performed using iPlan-apochromat 40×/1.3 NA oil immersion objective in Confocal Laser Scanning microscope. Image J software was used to calculate the fluorescence intensity. 500 cells were scored in each case.

Results: Immunostaining with anti-γ $H_2AX$ IgG shows that (1R,2R,5S)-1c causes DNA damage in MCF-7 cells as illustrated in FIG. 6A. The γ-$H_2AX$ intensity on treatment with (1R,2R,5S)-1c is shown in FIG. 6B. As seen from FIGS. 6A and 6B, the cells treated with (1R,2R,5S)-1c exhibit more DNA damage than compared to Cisplatin.

Example 22: Reactive Oxygen Species (ROS) Assay

Experiment: Reactive oxygen species (ROS) production in cells when treated with (1R,2R,5S)-1c, was estimated by ROS assay using 2',7'-dichlorodihydrofluorescein diacetate ($H_2DCFDA$). MCF-7 cells (5 mL) were seeded in 60 mm cell culture dishes at a density of $1.5 \times 10^5$ cells/mL. After cell attachment, they were incubated with 4 and 8 μM (1R,2R,5S)-1c for 24 h. Cells treated with 30 μM hydrogen peroxide was used as a positive control. Following 24 h of incubation, the cells were processed and analyzed using flow cytometry. The percentage of DCFH-DA positive MCF-7 cells in the absence and presence 4 and 8 μM (1R,2R,5S)-1c was determined by flow cytometry. 30 μM $H_2O_2$ was used as a positive control. Data are average of three independent set of experiments and ±indicates S.D.

Results: Intracellular ROS generation using dichlorofluoroscein-diacetate (DCFH-DA) assay in MCF-7 cells treated with media alone (negative control), 30 μM $H_2O_2$ (positive control), 4 and 8 μM (1R,2R,5S)-1c for 24 h is illustrated in FIG. 7A. The flow cytogram shows that ROS is generated in MCF-7 cells treated with (1R,2R,5S)-1c. Table 6 and FIG. 7B exhibits % of DCFH-DA positive cells after (1R,2R,5S)-1c treatment. As seen from FIG. 7B and Table 6, % of DCFH-DA positive MCF-7 cells is almost same from in cells treated with 8 μM (1R,2R,5S)-1c and positive control, 30 μM $H_2O_2$.

TABLE 6

Percentage of DCFH-DA positive MCF-7 cells after (1R,2R,5S)-1c treatment.

| S. No | Samples | % of DCFH-DA positive cells |
|---|---|---|
| 1 | Control | 1 ± 0.1 |
| 2 | 4 μM (1R,2R,5S)-1c | 49 ± 11 |
| 3 | 8 μM (1R,2R,5S)-1c | 74 ± 1 |
| 4 | 30 μM $H_2O_2$ | 72 ± 4 |

Example 23: Cell Cycle Analysis by Flow Cytometry

Experiment: MCF-7 cells (5 mL) were seeded in 60 mm cell culture dishes at a density of $1.5 \times 10^5$ cells/mL. The cells were incubated with 2 and 4 μM (1R,2R,5S)-1c for 36 h for cell cycle analysis. After the required incubation, cells were processed and analyzed by flow cytometry. Cell cycle data was analyzed using Flow Jo software. Cell cycle analysis and mitotic indices of MCF-7 cells in the absence and presence 2 and 4 μM (1R,2R,5S)-1c. Cell cycle analysis was done using flow cytometer after incubating the cells with PI. The data was analyzed using Flow Jo software. Data were average of three independent set of experiments with S.D (±). Mitotic index (percentage of cells in mitosis) was calculated based on DNA morphology of cells stained with Hoechst 33258. Data were average of three independent set of experiments with S.D (±). 1000 cells were scored in each set.

Results: DNA distribution profiles in different phases of the cell cycle after 36 h treatment with media alone (control) or 2 and 4 μM of (1R,2R,5S)-1c was determined by flow cytometry. FIG. 8A illustrates (1R,2R,5S)-1c blocked cells at the G2/M phase of the cell cycle. Effect of (1R,2R,5S)-1c on cell cycle progression of MCF-7 cells is shown in Table 7. Mitotic cells visualized based on DNA morphology after staining the cells with Hoechst 33258 show that (1R,2R,5S)-1c did not arrest cells at mitosis as illustrated in FIG. 8B. FIG. 8C graphically represents the mitotic index of MCF-7 cells in the absence and presence 2 and 4 μM (1R,2R,5S)-1c.

TABLE 7

Effect of (1R,2R,5S)-1c on cell cycle progression of MCF-7 cells.

| | | % of cells in different phases of cell cycle | | | Mitotic |
|---|---|---|---|---|---|
| S. No | Samples | G1 | S | G2/M | Index |
| 1 | Control | 60 ± 1 | 28 ± 2 | 10 ± 1 | 2 ± 1 |
| 2 | 2 μM (1R,2R,5S)-1c | 30 ± 2 | 31 ± 2 | 35 ± 2 | 3 ± 1 |
| 3 | 4 μM (1R,2R,5S)-1c | 18 ± 2 | 32 ± 3 | 50 ± 2 | 3.2 ± 1 |

Example 24: Assay to Study Effect on p53 and p21 Pathway

Experiment: MCF-7 ($5 \times 10^4$ cells/well) cells were seeded on glass cover slip in a 24-well cell culture plate. After the cells were attached, they were incubated with 4 and 8 μM (1R,2R,5S)-1c for 36 h, fixed with 3.7% formaldehyde and processed for immunostaining. After fixing, cells were blocked with 2% BSA and incubated with anti-p53 IgG (1:300) and anti-p21 IgG (1:300) for 2 h at 37° C. Primary antibody incubation was followed by Alexa Fluor 568-conjugated sheep anti-mouse secondary IgG (1:400) incubation for 1 h at 37° C. Hoechst 33258 was used to stain the DNA. Immunofluorescence images were captured using Eclipse TE 2000U microscope (Nikon, Tokyo, Japan) at 40× magnification and processed by Image-Pro Plus software (Media Cybernetics, Silver Spring, Md.). To determine the percentage of cells with nuclear accumulation of p53 and p21, 1000 cells were scored in each case. The experiment was repeated thrice.

Results: Immunostaining of cells with p53 and p21 antibodies show that (1R,2R,5S)-1c leads to the nuclear accumulation of p53 is shown in FIG. 9A. The left panel shows DNA of the cells stained with Hoechst 33258 (blue), the middle panel shows corresponding cells stained with anti-p53 IgG (red) and the right panel shows the merged image. (1R,2R,5S)-1c leads to nuclear accumulation of p53 which in turn transcriptionally activates p21, the downstream target of the p53 gene. Staining with anti-p21 antibody shows nuclear accumulation of p21 as shown in FIG. 9B. The left panel shows DNA of the cells stained with Hoechst 33258 (blue), the middle panel shows corresponding cells stained with anti-p21 IgG (red) and the right panel shows the merged image.

We claim:
1. A chiral N-heterocyclic carbene complex of formula (I):

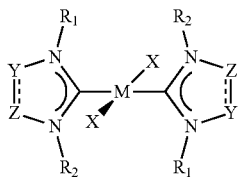

(I)

wherein,
M is palladium;
X is a monoanionic ligand selected from Br or OCOCF3;
R1 is a substituted or unsubstituted chiral hydrocarbyl selected from a group consisting of (1S) menthyl, (1R) menthyl, (1S, 2S, 5R) 2-i-propyl-5-methylcyclohexyl, (1R, 2R, 5S) 2-i-propyl-5-methylcyclohexyl, (1S)-pinane and (1R)-isobornyl;
R2 is selected from a group consisting of C1-C10 alkyl, allyl, aryl, heterocyclyl, alkylheterocyclyl;
Y or Z is N, CH or $CH_2$, with the proviso that any one of Y or Z is always N.

2. The chiral N-heterocyclic carbene complex as claimed in claim 1, wherein said compound is selected from:
(i)   trans-[1-(1S)-menthyl-4-(ethyl)-1,2,4-triazol-5-ylidene]$_2$PdBr$_2$ having formula (Ia):

Formula (Ia)

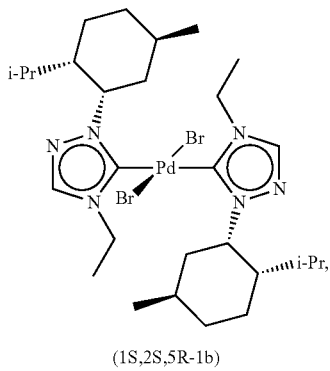

(1S,2S,5R-1b)

(ii)   trans-[1-(1R)-menthyl-4-(ethyl)-1,2,4-triazol-5-ylidene]$_2$PdBr$_2$ having formula (Ib):

Formula (Ib)

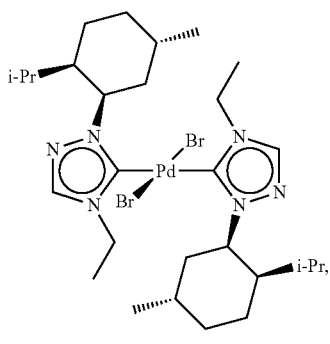

(1R,2R,5S-1b)

(iii)   trans-[1-(1S)-menthyl-4-(allyl)-1,2,4-triazol-5-ylidene]$_2$PdBr$_2$ having formula (Ic):

Formula (Ic)

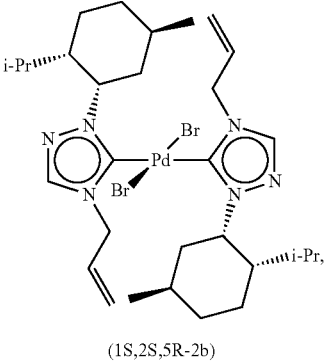

(1S,2S,5R-2b)

(iv)   trans-[1-(1R)-menthyl-4-(allyl)-1,2,4-triazol-5-ylidene]$_2$PdBr$_2$ having formula (Id):

Formula (Id)

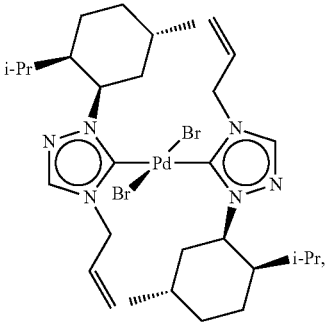

(1R,2R,5S-2b)

(v)   trans-[1-(1S)-menthyl-4-(benzyl)-1,2,4-triazol-5-ylidene]$_2$PdBr$_2$ having formula (Ie):

Formula (Ie)

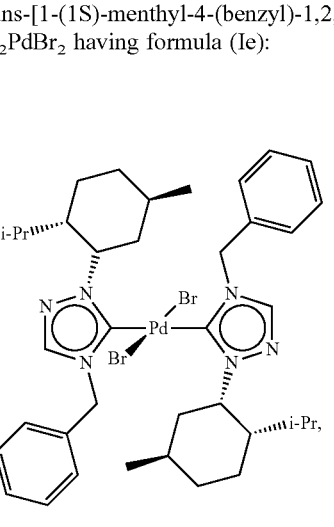

(1S,2S,5R-3b)

(vi)   trans-[1-(1R)-menthyl-4-(benzyl)-1,2,4-triazol-5-ylidene]$_2$PdBr$_2$ having formula (If):

Formula (If)

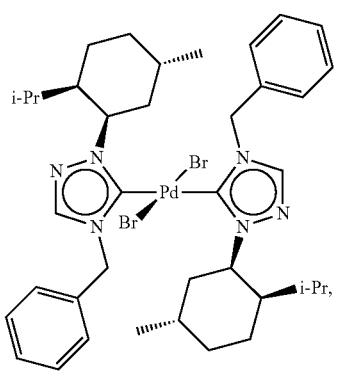

(1R,2R,5S-3b)

(vii) trans-[1-(1S)-menthyl-4-(ethyl)-1,2,4-triazol-5-ylidene]$_2$Pd(OCOCF$_3$)$_2$ having a formula (Ig):

Formula (Ig)

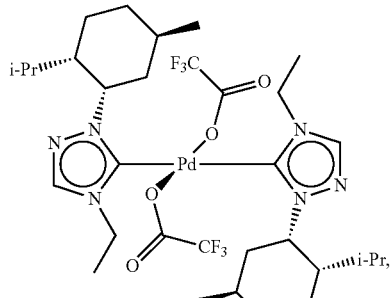

(1S,2S,5R-1c)

(viii) trans-[1-(1R)-menthyl-4-(ethyl)-1,2,4-triazol-5-ylidene]$_2$Pd(OCOCF$_3$)$_2$ having a formula (Ih):

Formula (Ih)

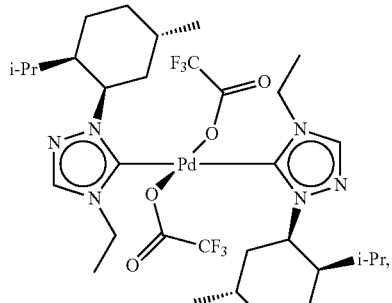

(1R,2R,5S-1c)

(ix) trans-[1-(1S)-menthyl-4-(benzyl)-1,2,4-triazol-5-ylidene]$_2$Pd(OCOCF$_3$)$_2$ having a formula (Ii):

Formula (Ii)

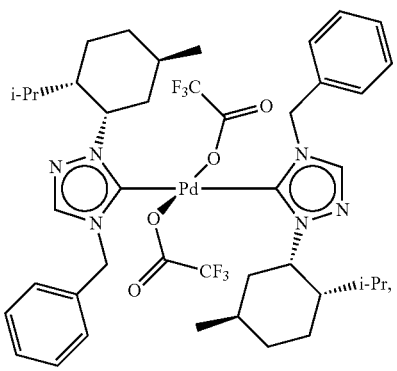

(1S,2S,5R-3c)

(x) trans-[1-(1R)-menthyl-4-(benzyl)-1,2,4-triazol-5-ylidene]$_2$Pd(OCOCF$_3$)$_2$ having a formula (Ij):

Formula (Ij)

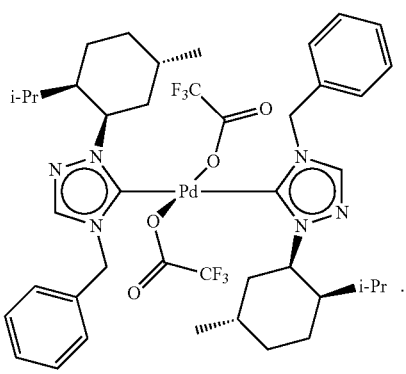

(1R,2R,5S-3c)

3. The chiral N-heterocyclic carbene complex as claimed in claim 2 which is (vii) trans-[1-(1S)-menthyl-4-(ethyl)-1,2,4-triazol-5-ylidene]$_2$Pd(OCOCF$_3$)$_2$ having a formula (Ig):

Formula (Ig)

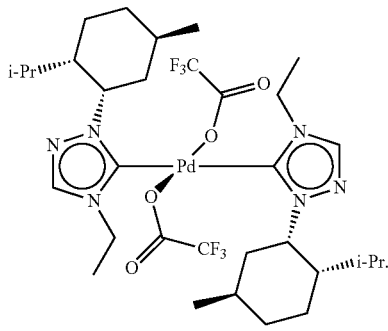

(1S,2S,5R-1c)

4. The chiral N-heterocyclic carbene complex as claimed in claim 2 which is (viii) trans-[1-(1R)-menthyl-4-(ethyl)-1,2,4-triazol-5-ylidene]$_2$Pd(OCOCF$_3$)$_2$ having a formula (Ih):

Formula (Ih)

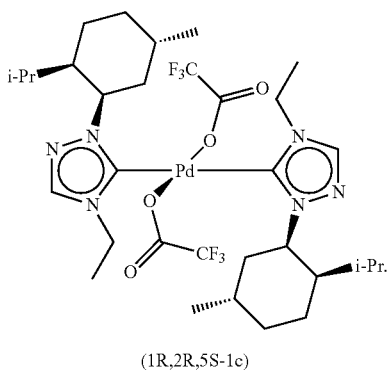

(1R,2R,5S-1c)

5. The chiral N-heterocyclic carbene complex as claimed in claim 1 which is effective against cancer.

6. The chiral N-heterocyclic carbene complex as claimed in claim 5, wherein the cancer is breast cancer, cervical cancer, lung cancer, skin cancer, or multi drug resistant cancer.

7. A pharmaceutical composition comprising the chiral N-heterocyclic carbene complex as claimed in claim 1, along with a pharmaceutically acceptable excipient.

8. The pharmaceutical composition as claimed in claim 7, wherein the said chiral N-heterocyclic carbene complex is one or more selected from:
 (i) trans-[1-(1S)-menthyl-4-(ethyl)-1,2,4-triazol-5-ylidene]$_2$PdBr$_2$;
 (ii) trans-[1-(1R)-menthyl-4-(ethyl)-1,2,4-triazol-5-ylidene]$_2$PdBr$_2$;
 (iii) trans-[1-(1S)-menthyl-4-(allyl)-1,2,4-triazol-5-ylidene]$_2$PdBr$_2$;
 (iv) trans-[1-(1R)-menthyl-4-(allyl)-1,2,4-triazol-5-ylidene]$_2$PdBr$_2$;
 (v) trans-[1-(1S)-menthyl-4-(benzyl)-1,2,4-triazol-5-ylidene]$_2$PdBr$_2$;
 (vi) trans-[1-(1R)-menthyl-4-(benzyl)-1,2,4-triazol-5-ylidene]$_2$PdBr$_2$;
 (vii) trans-[1-(1S)-menthyl-4-(ethyl)-1,2,4-triazol-5-ylidene]$_2$Pd(OCOCF$_3$)$_2$;
 (viii) trans-[1-(1R)-menthyl-4-(ethyl)-1,2,4-triazol-5-ylidene]$_2$Pd(OCOCF$_3$)$_2$;
 (ix) trans-[1-(1S)-menthyl-4-(benzyl)-1,2,4-triazol-5-ylidene]$_2$Pd(OCOCF$_3$)$_2$; and
 (x) trans-[1-(1R)-menthyl-4-(benzyl)-1,2,4-triazol-5-ylidene]$_2$Pd(OCOCF$_3$)$_2$.

9. The pharmaceutical composition as claimed in claim 8 which is for treating cancer.

10. A process for preparation of the enantiomeric pairs of N-heterocyclic carbene complex as claimed in claim 1 comprising steps of: (a) converting a chiral alcohol using a tosylating agent so as to make a leaving group; followed by a (b) nucleophilic substitution reaction of the tosylated chiral hydrocarbyl (R1-OTs) formed in step 'a' with a heterocyclic compound by a suitable base; (c)N-alkylation of the compound formed in step 'b' with selective alkyl halides (R2-X) to give respective azolium salts; (d) directly reacting the formed azolium salts with a metallic salt MX$_2$, wherein, M is Pd, X is a monoanionic ligand selected from Br, or OCOCH$_3$, in presence of a suitable base at temperature under reflux conditions forming the present (NHC)$_2$MX$_2$ type chiral precursors; followed by (e) a metal salt metathesis reaction of said (NHC)$_2$MX$_2$ type chiral precursors wherein, M is Pd, X is selected from Br, Cl, I or OCOCH$_3$, with M'nYn, wherein M' is any metal, Y is any anionic ligand, n is 1 or 2, under stirring in room temperature.

11. The process as claimed in claim 10, wherein the leaving group is selected from trifluoromethane sulfonate (CF$_3$SO$_3$), para-toluene sulfonate, tosylate (OTs), methane sulfonate, mesylate (Ms), para-nitrophenyl sulfonate, nosylate (Ns), para-bromophenyl sulfonate, brosylate (Bs), carboxylate (OCOR) and phenoxides (OAr).

12. The process as claimed in claim 10, wherein chiral hydrocarbyl is selected from (1S) menthyl, (1R) menthyl, (1S, 2S, 5R) 2-i-propyl-5-methylcyclohexyl, (1R, 2R, 5S) 2-i-propyl-5-methylcyclohexyl, (1S)-pinane and (1R)-isobornyl.

13. The process as claimed in claim 10, wherein the heterocycle is selected from a group consisting of 1,2,4-triazole, 1,2,3-triazole and tetrazole.

14. The process as claimed in claim 10, wherein the alkyl halide is selected from ethyl bromide, allyl bromide and benzyl bromide.

15. The process as claimed in claim 10, wherein base is selected from triethyl amine Et$_3$N, NaH, KOtBu, K$_2$CO$_3$ and Na$_2$CO$_3$.

16. The process as claimed in claim 10, wherein the metal salt is selected from AgOCOCF$_3$, LiOCOCF$_3$, NaOCOCF$_3$, KOCOCF$_3$ and NH$_4$OCOCF$_3$.

17. A process for preparation of the enantiomeric pairs of N-heterocyclic carbene complex as claimed in claim 1 comprising steps of: (a) converting a chiral alcohol using a tosylating agent so as to make a leaving group; followed by a (b) nucleophilic substitution reaction of the tosylated chiral hydrocarbyl (R1-OTs) formed in step 'a' with a heterocyclic compound by a suitable base; (c)N-alkylation of the compound formed in step 'b' with selective alkyl halides (R2-X) to give respective azolium salts; (d) directly reacting the formed azolium salts with a metallic salt MX$_2$, wherein, M is Pd, X is a monoanionic ligand selected from Br, or OCOCH3, in presence of a suitable base at temperature under reflux conditions forming the present (NHC)2MX2 type chiral precursors; followed by (e) a metal salt metathesis reaction of said (NHC)2MX2 type chiral precursors wherein, M is Pd, X is selected from Br, Cl, I or OCOCH3, with M'nYn, wherein M' is any metal, Y is OCOCF3, n is 1 or 2, under stirring in room temperature.

18. A method of treating cancer comprising administering a chiral N-heterocyclic carbene complex of formula (I):

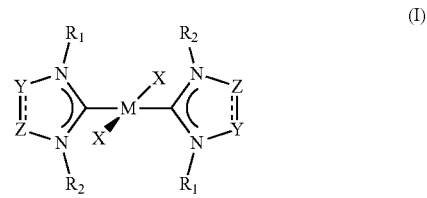

wherein,
M is palladium;
X is a monoanionic ligand selected from Br or OCOCF$_3$;
R1 is a substituted or unsubstituted chiral hydrocarbyl selected from a group consisting of (1S) menthyl, (1R) menthyl, (1S, 2S, 5R) 2-i-propyl-5-methylcyclohexyl, (1R, 2R, 5S) 2-i-propyl-5-methylcyclohexyl, (1S)-pinane and (1R)-isobornyl;
R2 is selected from a group consisting of C1-C10 alkyl, allyl, aryl, heterocyclyl, alkylheterocyclyl;

Y or Z is N, CH or CH$_2$, with the proviso that any one of Y or Z is always N,
or a pharmaceutical composition comprising the chiral N-heterocyclic carbene complex.

19. The method as claimed in claim 18, wherein the chiral N-heterocyclic carbene complex or the pharmaceutical composition is selective towards the cancer cells.

20. The method as claimed in claim 18, wherein the chiral N-heterocyclic carbene complex or the pharmaceutical composition results in apoptosis of cancer cells by cleavage of PARP.

21. The method as claimed in claim 18, wherein the chiral N-heterocyclic carbene complex or the pharmaceutical composition results in DNA damage in the nucleus of the cancer cells.

22. The method as claimed in claim 18, wherein the chiral N-heterocyclic carbene complex or the pharmaceutical composition results in cancer cell death by the production of reactive oxygen species.

23. The method as claimed in claim 18, wherein the chiral N-heterocyclic carbene complex or the pharmaceutical composition causes ceasing of cancer cell growth at the G2 phase cell cycle.

24. The method as claimed in claim 18, wherein the chiral N-heterocyclic carbene complex or the pharmaceutical composition results in alteration in the p53 dependent pathway in cancer cells.

* * * * *